(12) United States Patent
Glicksman et al.

(10) Patent No.: US 8,545,557 B2
(45) Date of Patent: Oct. 1, 2013

(54) HUMAN IMPLANTABLE TISSUE EXPANDER

(75) Inventors: Avraham Glicksman, Petah Tikva (IL); Efraim Ramon, Be'er Ya'akov (IL)

(73) Assignee: Implite Ltd, Petah Tikva (IL)

( * ) Notice: Subject to any disclaimer, the term of this patent is extended or adjusted under 35 U.S.C. 154(b) by 701 days.

(21) Appl. No.: 12/521,126

(22) PCT Filed: Dec. 31, 2007

(86) PCT No.: PCT/IL2007/001629
§ 371 (c)(1),
(2), (4) Date: Jan. 7, 2010

(87) PCT Pub. No.: WO2008/081439
PCT Pub. Date: Jul. 10, 2008

(65) Prior Publication Data
US 2010/0114312 A1    May 6, 2010

Related U.S. Application Data

(60) Provisional application No. 60/878,564, filed on Jan. 3, 2007.

(51) Int. Cl.
*A61F 2/12* (2006.01)
*A61F 2/52* (2006.01)
*A61M 29/00* (2006.01)

(52) U.S. Cl.
USPC .................................. 623/8; 623/7; 606/192

(58) Field of Classification Search
CPC ............. A61M 29/00; A61F 2/12; A61F 2/52
USPC ............. 623/8, 17.12; 5/665–688; 606/192
See application file for complete search history.

(56) References Cited

U.S. PATENT DOCUMENTS

| | | | | |
|---|---|---|---|---|
| 3,366,975 A | * | 2/1968 | Pangman | 623/8 |
| 3,986,213 A | | 10/1976 | Lynch | |
| 4,430,764 A | * | 2/1984 | Finkelstein | 5/682 |
| 4,624,671 A | | 11/1986 | Kress | |
| 4,651,717 A | | 3/1987 | Jakubczak | |
| 4,685,447 A | * | 8/1987 | Iversen et al. | 128/899 |
| 5,060,328 A | * | 10/1991 | Larson | 5/683 |
| 5,074,878 A | * | 12/1991 | Bark et al. | 623/8 |
| 5,104,409 A | | 4/1992 | Baker | |
| 5,110,653 A | * | 5/1992 | Landi | 428/116 |
| 5,122,405 A | * | 6/1992 | Landi | 428/116 |
| 5,137,769 A | * | 8/1992 | Landi | 428/116 |
| 5,159,725 A | * | 11/1992 | Larson | 5/683 |
| 5,180,619 A | * | 1/1993 | Landi et al. | 428/116 |

(Continued)

FOREIGN PATENT DOCUMENTS

| | | |
|---|---|---|
| FR | 2 859 098 A1 | 3/2005 |
| FR | 2 862 523 A1 | 5/2005 |

(Continued)

*Primary Examiner* — Andrew Iwamaye
(74) *Attorney, Agent, or Firm* — Browdy and Neimark, PLLC

(57) ABSTRACT

An implantable tissue expander including an internal skeletal element extending between a base surface and an outer surface and including at least one plurality of elongate cells extending along mutually generally parallel axes from the base surface to the outer surface and being defined by elongate cell walls formed of a resilient material and a sealed enclosure, sealing the internal skeletal element and adapted for preventing body fluids from filling the plurality of elongate cells.

23 Claims, 25 Drawing Sheets

(56) References Cited

U.S. PATENT DOCUMENTS

| | | | |
|---|---|---|---|
| 5,203,607 A * | 4/1993 | Landi | 297/214 |
| 5,340,352 A * | 8/1994 | Nakanishi et al. | 450/57 |
| 5,358,521 A | 10/1994 | Shane | |
| 5,496,367 A | 3/1996 | Fisher | |
| 5,496,610 A * | 3/1996 | Landi et al. | 428/73 |
| 5,500,019 A | 3/1996 | Johnson et al. | |
| 5,509,484 A * | 4/1996 | Landi et al. | 168/14 |
| 5,534,343 A * | 7/1996 | Landi et al. | 428/313.5 |
| 5,545,217 A | 8/1996 | Offray et al. | |
| 5,617,595 A * | 4/1997 | Landi et al. | 5/653 |
| 5,701,621 A * | 12/1997 | Landi et al. | 5/691 |
| 5,824,081 A | 10/1998 | Knapp et al. | |
| 5,836,871 A | 11/1998 | Wallace | |
| 5,840,397 A * | 11/1998 | Landi et al. | 428/73 |
| 5,840,400 A * | 11/1998 | Landi et al. | 428/116 |
| 5,961,552 A * | 10/1999 | Iversen et al. | 623/8 |
| 6,066,220 A | 5/2000 | Schneider-Nieskens | |
| 6,206,930 B1 * | 3/2001 | Burg et al. | 623/23.64 |
| 6,214,045 B1 | 4/2001 | Corbitt, Jr. et al. | |
| 6,228,116 B1 | 5/2001 | Ledergerber | |
| 6,315,796 B1 | 11/2001 | Eaton | |
| 6,415,583 B1 * | 7/2002 | Landi et al. | 54/65 |
| 6,432,138 B1 | 8/2002 | Offray | |
| 6,544,287 B1 | 4/2003 | Johnson et al. | |
| 6,605,116 B2 | 8/2003 | Falcon et al. | |
| 6,802,861 B1 | 10/2004 | Hamas | |
| 6,811,570 B1 | 11/2004 | Gehl | |
| 2001/0010024 A1 | 7/2001 | Ledergerber | |
| 2002/0143396 A1 * | 10/2002 | Falcon et al. | 623/8 |
| 2003/0074084 A1 | 4/2003 | Nakao | |
| 2004/0148024 A1 | 7/2004 | Williams | |
| 2004/0176841 A1 | 9/2004 | Ferguson | |
| 2006/0264399 A1 | 11/2006 | Lim et al. | |
| 2009/0093878 A1 | 4/2009 | Glicksman | |

FOREIGN PATENT DOCUMENTS

| | | |
|---|---|---|
| WO | 98/10803 A1 | 3/1998 |
| WO | 99/20319 A1 | 4/1999 |
| WO | 01/66039 A1 | 9/2001 |
| WO | 2008/038851 A1 | 4/2003 |
| WO | 2006/114786 A2 | 11/2006 |
| WO | 2008/081439 A2 | 7/2008 |

* cited by examiner

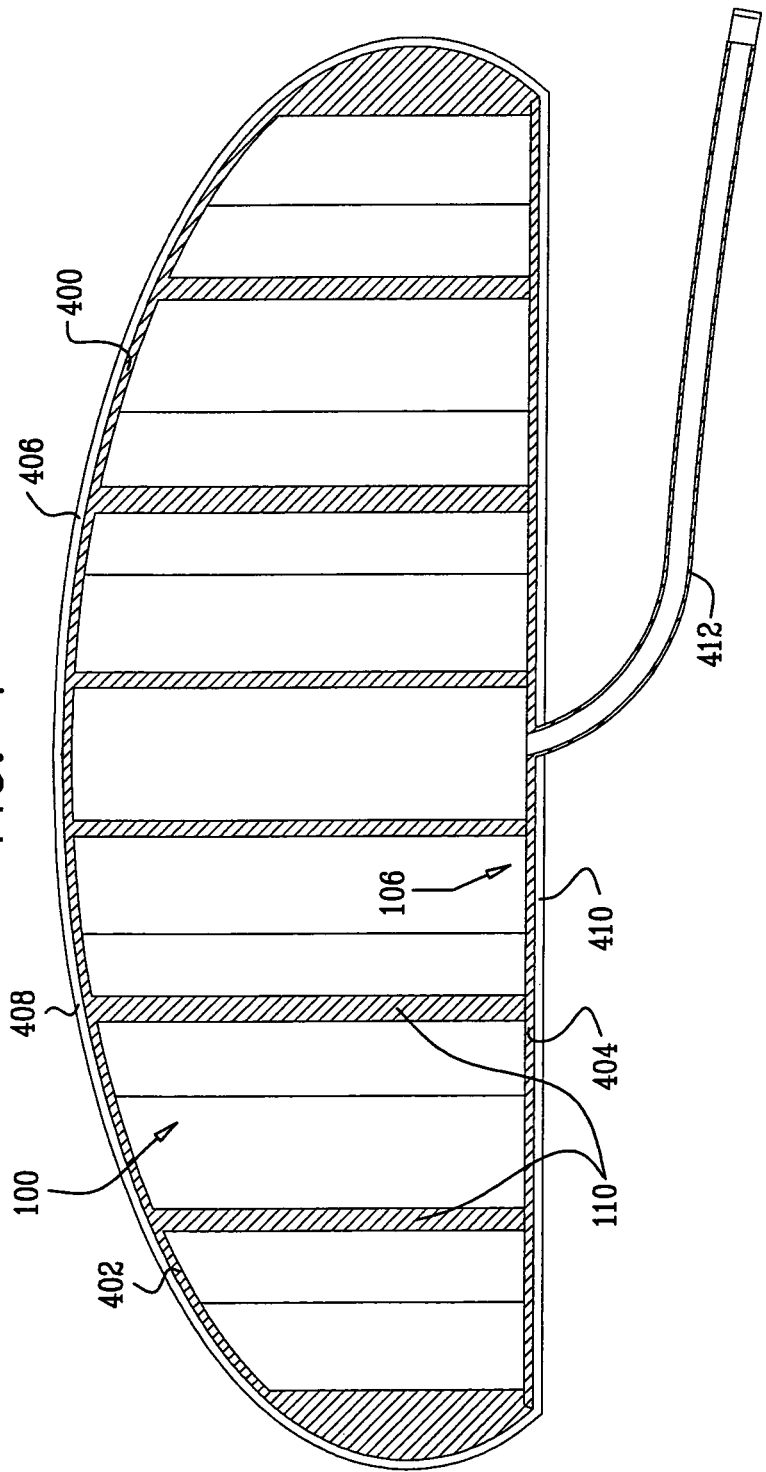

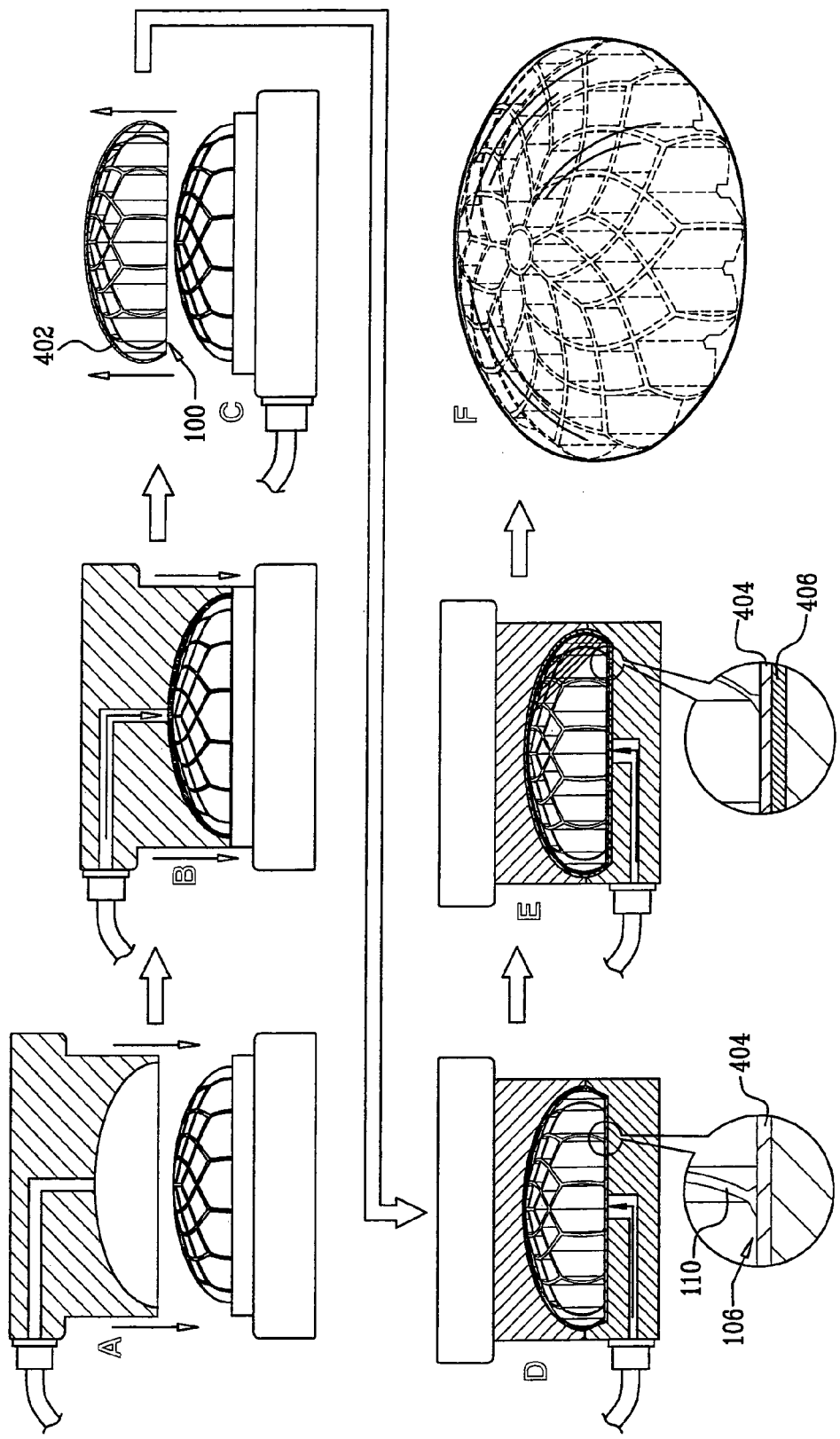

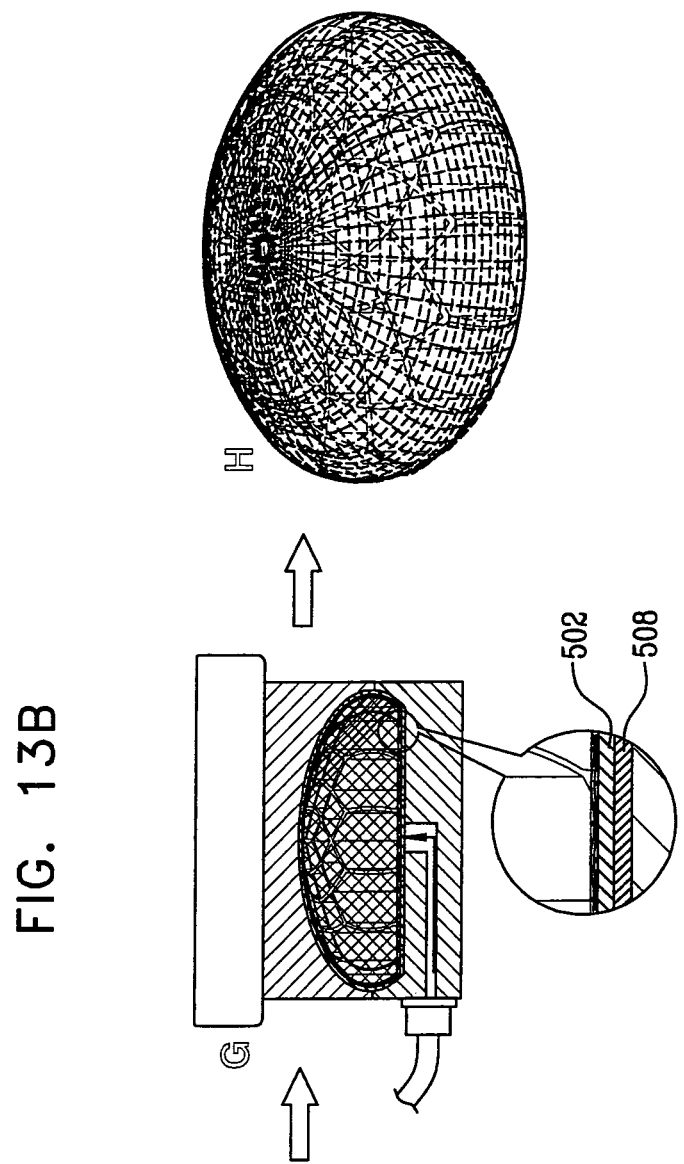

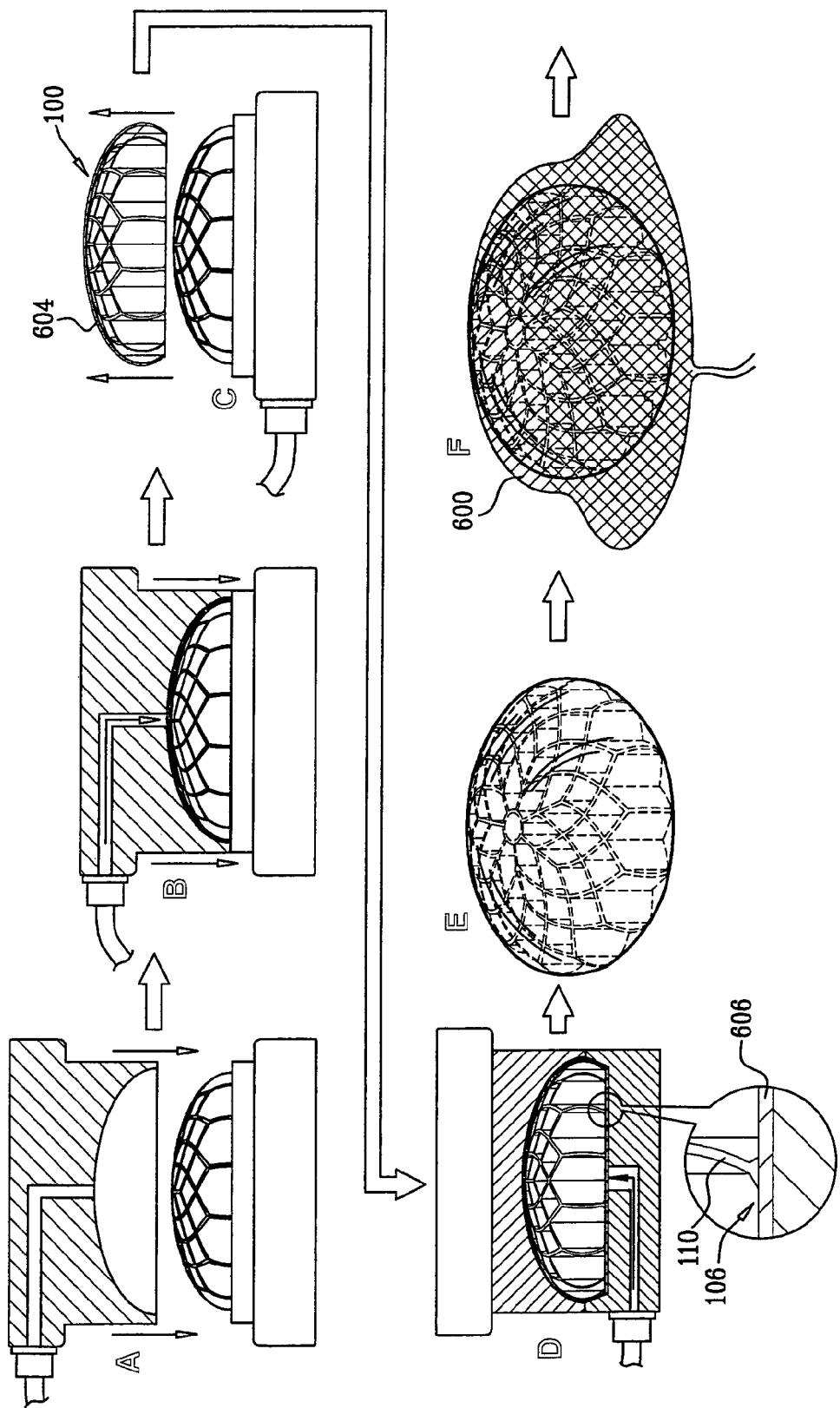

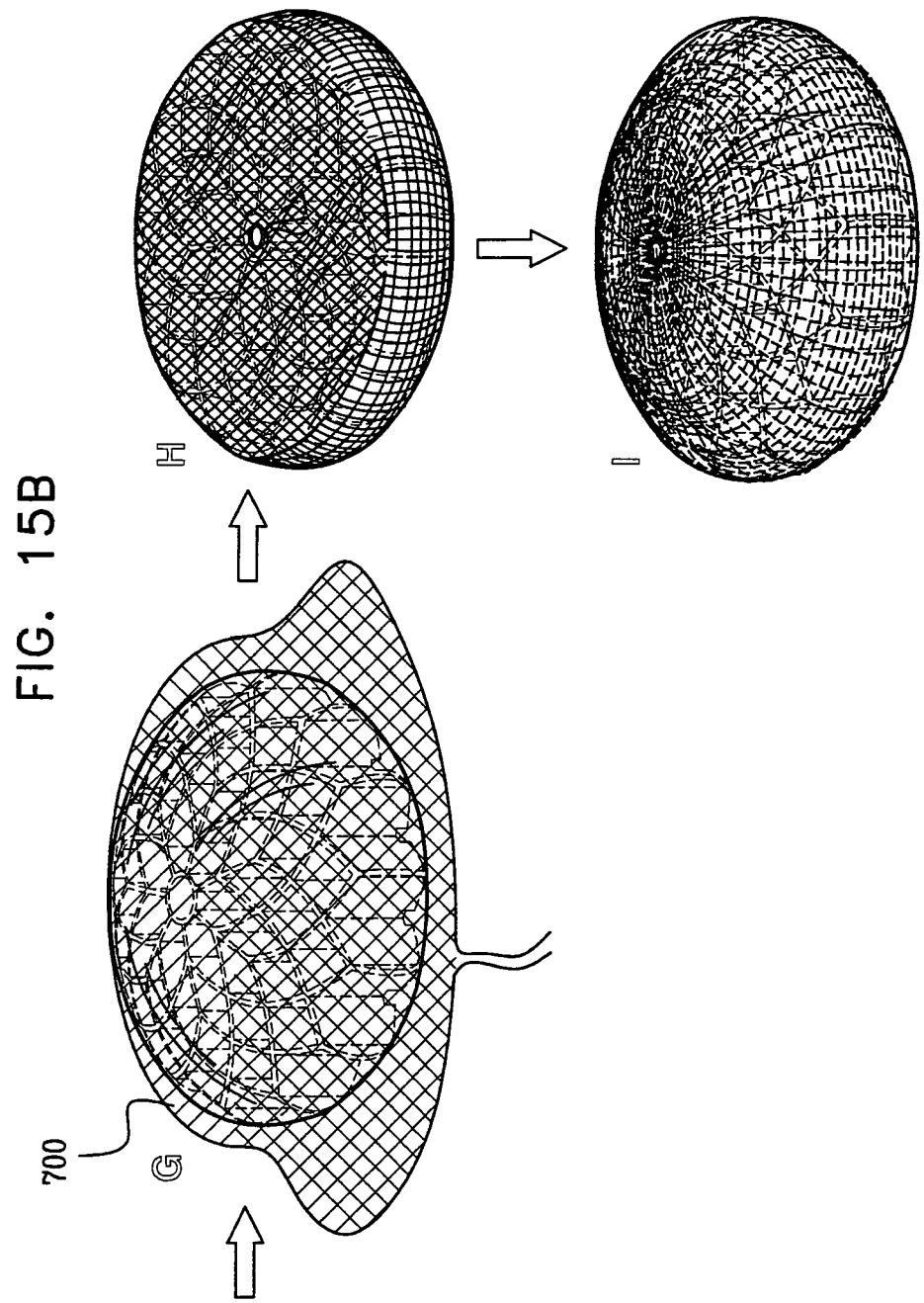

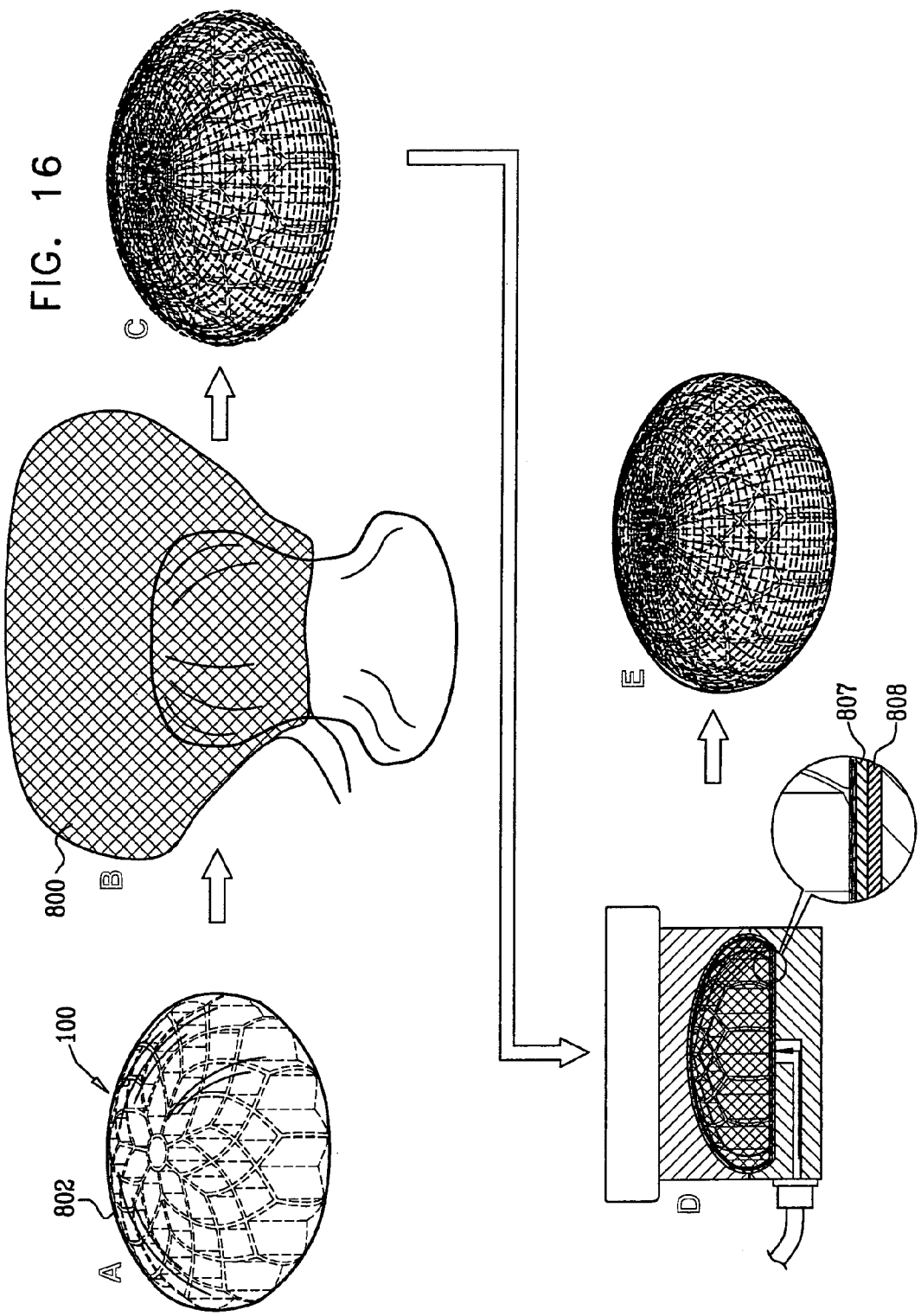

HUMAN IMPLANTABLE TISSUE EXPANDER

REFERENCE TO RELATED APPLICATIONS

Reference is made to U.S. Provisional Patent Application Ser. No. 60/878,564, filed Jan. 3, 2007 and entitled "Human Implantable Tissue Expander," the disclosure of which is hereby incorporated by reference and priority of which is hereby claimed pursuant to 37 CFR 1.78(a) (4) and (5)(i).

FIELD OF THE INVENTION

The present invention relates to implantable tissue expanders generally.

BACKGROUND OF THE INVENTION

The following published patent documents are believed to represent the current state of the art:
U.S. Pat. Nos. 6,315,796 and 6,605,116, and
U.S. Published Patent Application Nos. 2001/0010024; 2003/0074084 and 2004/0148024.

SUMMARY OF THE INVENTION

The present invention relates to implantable tissue expanders.

There is thus provided in accordance with a preferred embodiment of the present invention an implantable tissue expander including an integrally formed internal skeletal element extending between a base surface and an outer surface and including at least one plurality of elongate cells extending along mutually generally parallel axes from the base surface to the outer surface and being mutually defined by elongate cell walls formed of a resilient material and a sealed enclosure, sealing the internal skeletal element and adapted for preventing body fluids from filling the plurality of elongate cells.

Preferably, the at least one plurality of elongate cells includes at least first and second pluralities of elongate cells extending over correspondingly different mutually generally parallel axes from the base surface to the outer surface. Alternatively, the at least one plurality of elongate cells includes a single plurality of elongate cells extending over mutually generally parallel axes from the base surface to the outer surface.

Preferably, the base surface is generally flat. Additionally or alternatively; the outer surface is generally convex.

Preferably, the elongate cell walls define fluid passageways communicating between adjacent cells in the at least one plurality of elongate cells. Additionally or alternatively, the at least one plurality of elongate cells includes a central cylindrical cell.

Preferably, the elongate cell walls are of generally uniform thickness. Additionally or alternatively, the at least one plurality of elongate cells includes partial cells located along the periphery thereof. Preferably, the partial cells are identical. Preferably, the elongate cells have a hexagonal cross section.

Preferably, the implantable tissue expander includes at least one mesh. Additionally, the at least one mesh is formed of a highly deformable, minimally stretchable material. Additionally or alternatively, the at least one mesh is at least partially integrated with the sealed enclosure.

Preferably, the at least one mesh includes a plurality of layers of mesh. Additionally, at least two layers of mesh are located on opposite sides of at least one layer of the sealed enclosure.

Preferably, the sealed enclosure includes a generally convex portion and a base portion. Additionally or alternatively, the sealed enclosure includes multiple enclosure layers.

Preferably, the implantable tissue expander also includes a tube communicating with the interior of the sealed enclosure. Additionally or alternatively, the sealed enclosure has non-uniform wall thickness.

There is also provided in accordance with another preferred embodiment of the present invention a method of manufacturing an implantable tissue expander including forming an internal skeletal element, the internal skeletal element extending between a base surface and an outer surface and including at least one plurality of elongate cells extending along mutually generally parallel axes from the base surface to the outer surface and being defined by elongate cell walls formed of a resilient material and forming a peripheral enclosure over the internal skeletal element, the peripheral enclosure being operative to seal the internal skeletal element and being adapted to prevent body fluids from filling the plurality of elongate cells.

Preferably, the forming a peripheral enclosure includes forming a base portion of the enclosure and a generally convex portion of the enclosure and polymerizing the base portion together with the periphery of the generally convex portion and with edges of the elongate cell walls.

Preferably, the method also includes forming an outer enclosure over the peripheral enclosure. Additionally or alternatively, the forming steps include integrally forming the internal skeletal element and a generally convex portion of the peripheral enclosure over a mesh.

Preferably, the method also includes providing a tube communicating with the interior of the peripheral enclosure.

BRIEF DESCRIPTION OF THE DRAWINGS

The present invention will be understood and appreciated more fully from the following detailed description, taken in conjunction with the drawings in which:

FIG. 4 is a sectional illustration of an implantable tissue expander employing an internal skeletal element and constructed and operative in accordance with one embodiment of the present invention;

FIG. 12 is a simplified illustration of a method of manufacturing the implantable tissue expander of FIG. 4 in accordance with an embodiment of the invention;

FIGS. 13A and 13B together are a simplified illustration of a method of manufacturing the implantable tissue expander of FIG. 5 in accordance with another embodiment of the present invention;

FIGS. 14A and 14B together are a simplified illustration of a method of manufacturing the implantable tissue expander of FIG. 6 in accordance with yet another embodiment of the present invention;

FIGS. 15A and 15B together are a simplified illustration of a method of manufacturing the implantable tissue expander of FIG. 7 in accordance with still another embodiment of the present invention;

FIG. 16 is a simplified illustration of a method of manufacturing the implantable tissue expander of FIG. 8 in accordance with a further embodiment of the present invention;

DETAILED DESCRIPTION OF PREFERRED EMBODIMENTS

Reference is now made to FIGS. 1A, 1B, 1C and 1D, which are, respectively, pictorial top view, pictorial bottom view, first sectional and second sectional illustrations of an integrally formed internal skeletal element 100 employed in an implantable tissue expander in accordance with a preferred embodiment of the present invention.

Figure 1A:
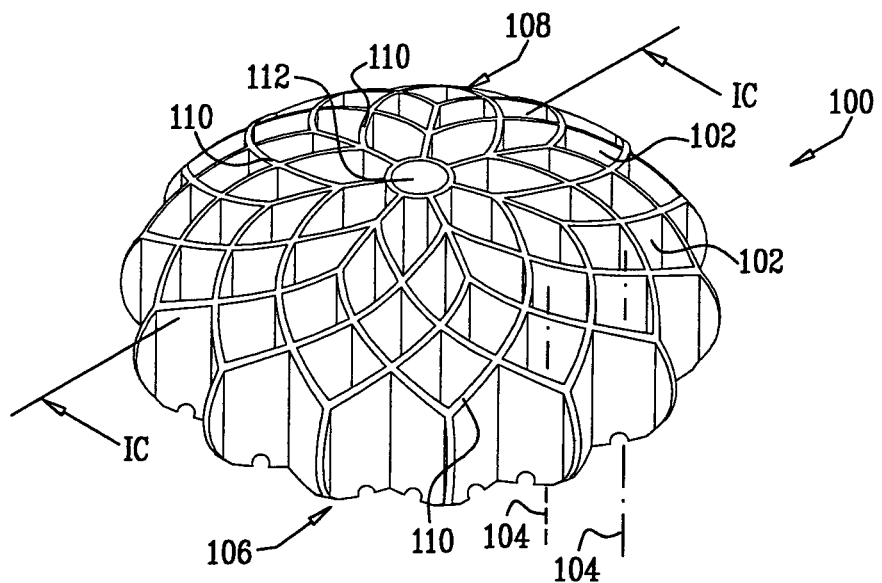
FIGS. 1A, 1B, 1C and 1D are, respectively, pictorial top view, pictorial bottom view, first sectional and second sectional illustrations of an integrally formed internal skeletal element employed in an implantable tissue expander in accordance with a preferred embodiment of the present invention.
Figure 1B:
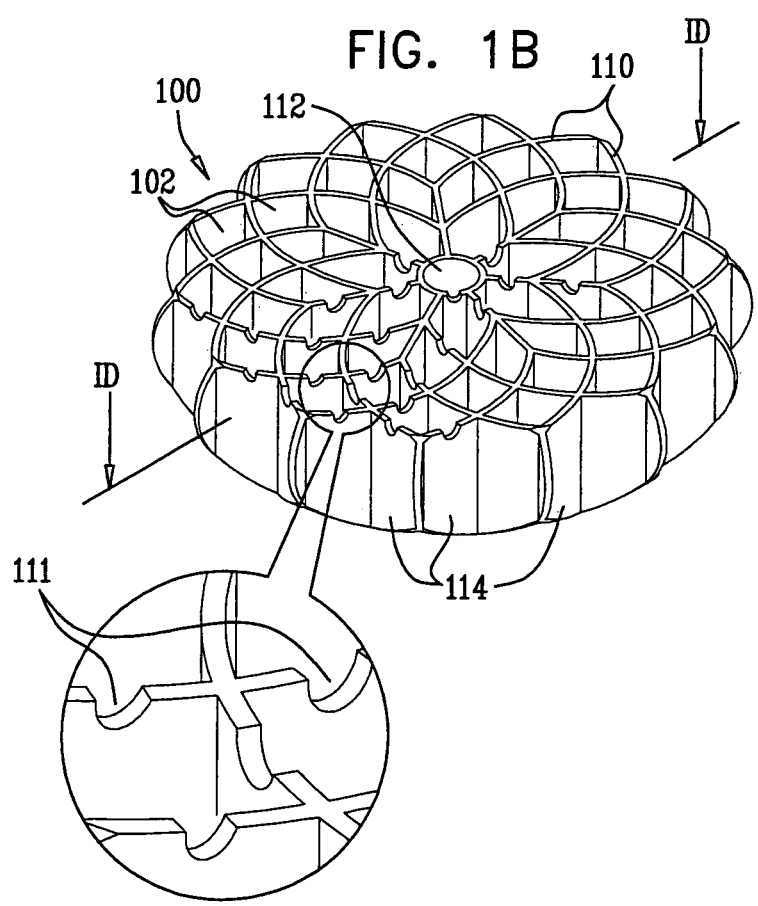
Figure 1C:
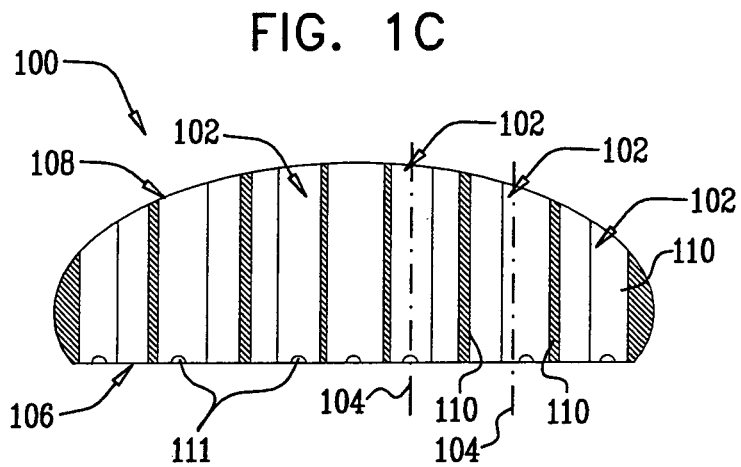
Figure 1D:
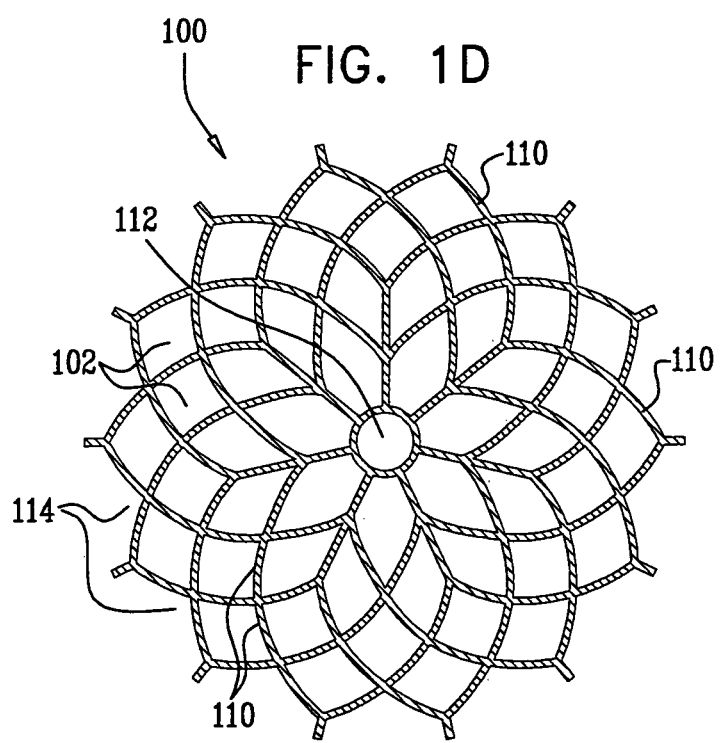
Figure 2A:
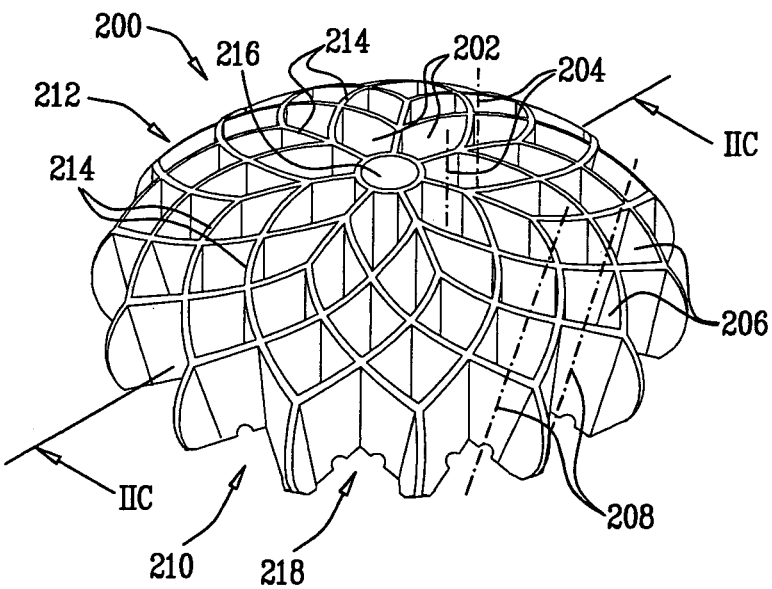
FIGS. 2A, 2B, 2C and 2D are, respectively, pictorial top view, pictorial bottom view, first sectional and second sectional illustrations of an integrally formed internal skeletal element employed in an implantable tissue expander in accordance with another preferred embodiment of the present invention.
Figure 2B:
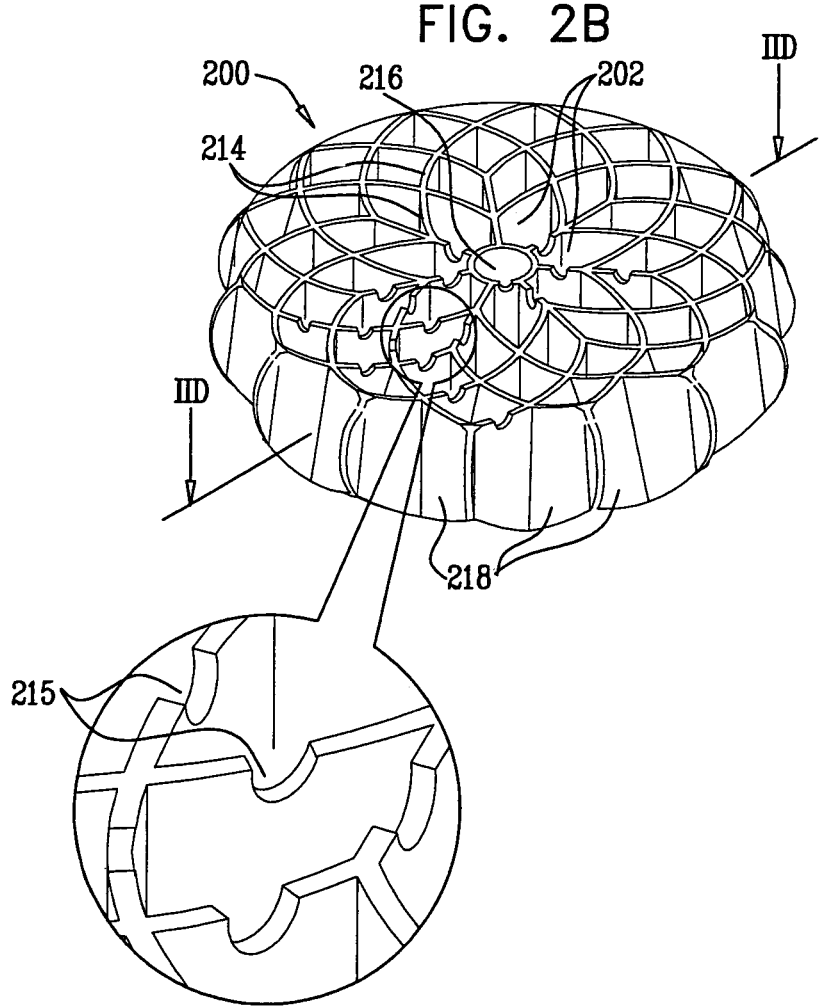
Figure 2C:
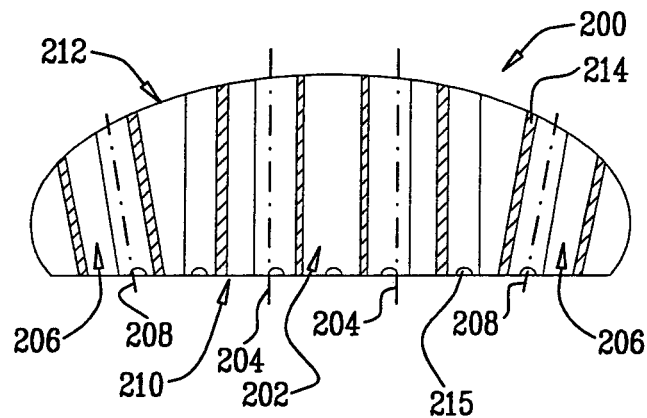
Figure 2D:
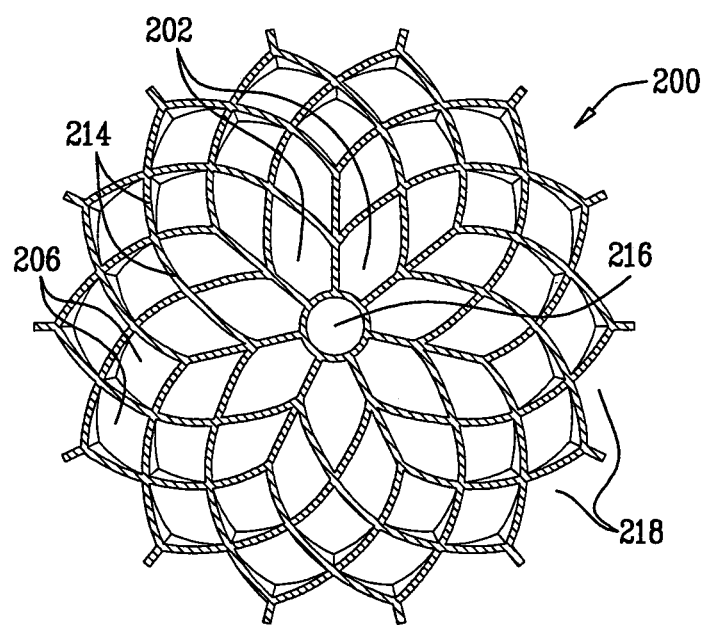

As seen in FIGS. 1A-1D, the integrally formed internal skeletal element 100 includes an array of elongate cells 102 extending along mutually generally parallel axes 104 from an imaginary base surface 106, which is typically flat, as in the illustrated embodiment, to an imaginary outer surface 108, which is preferably generally convex and is tucked in adjacent the imaginary base surface 106 as seen clearly in FIGS. 1A-1C. Elongate cells 102 are mutually defined by elongate cell walls 110 formed of a resilient material. Elongate cell walls 110 are preferably formed so as to define fluid passageways 111 communicating between adjacent cells 102. The internal skeletal element 100 is capable of independently exhibiting a defined, convex, three-dimensional shape.

In the illustrated embodiment, the array of elongate cells 102 is preferably characterized in that it includes a central cylindrical cell 112 and that elongate cell walls 110 are of generally uniform thickness. It is also characterized in that a regular pattern of partial cells 114 are located along the periphery of the array. In the illustrated embodiment of FIGS. 1A-1D, all of the partial cells 114 are identical. In other embodiments, this is not necessarily the case. Alternatively, the elongate well walls 110 need not be of generally uniform thickness and may be of different thicknesses and/or varying thickness.

Reference is now made to FIGS. 2A, 2B, 2C and 2D, which are respectively pictorial top view, pictorial bottom view, first sectional and second sectional illustrations of an integrally formed internal skeletal element 200 employed in an implantable tissue expander in accordance with a preferred embodiment of the present invention.

As seen in FIGS. 2A-2D, the integrally formed internal skeletal element 200 includes an array of elongate cells including a first plurality of elongate cells 202 at the center of the array, which cells 202 extend along mutually generally parallel axes 204 and a second plurality of elongate cells 206, each of which extends along an axis 208 which is splayed outwardly with respect to axes 204. Cells 202 and 206 extend from an imaginary base surface 210, which is typically flat, as in the illustrated embodiment, to an imaginary outer surface 212, which is preferably generally convex and is tucked in adjacent the imaginary base surface 210 as seen in FIGS. 2A-2D. Elongate cells 202 and 206 are mutually defined by elongate cell walls 214 formed of a resilient material. Elongate cell walls 214 are preferably formed so as to define fluid passageways 215 communicating between adjacent cells 202 and 206.

In the illustrated embodiment, the array of elongate cells 202 is preferably characterized in that it includes a central cylindrical cell 216 and that elongate cell walls 214 are of generally uniform thickness. It is also characterized in that a regular pattern of partial cells 218 are located along the periphery of the array. In the illustrated embodiment of FIGS. 2A-2D, all of the partial cells 218 are identical. In other embodiments, this is not necessarily the case.

Reference is now made to FIGS. 3A, 3B, 3C and 3D, which are respectively pictorial top view, pictorial bottom view, first sectional and second sectional illustrations of an integrally formed internal skeletal element 300 employed in an implantable tissue expander in accordance with a preferred embodiment of the present invention.

Figure 3A:
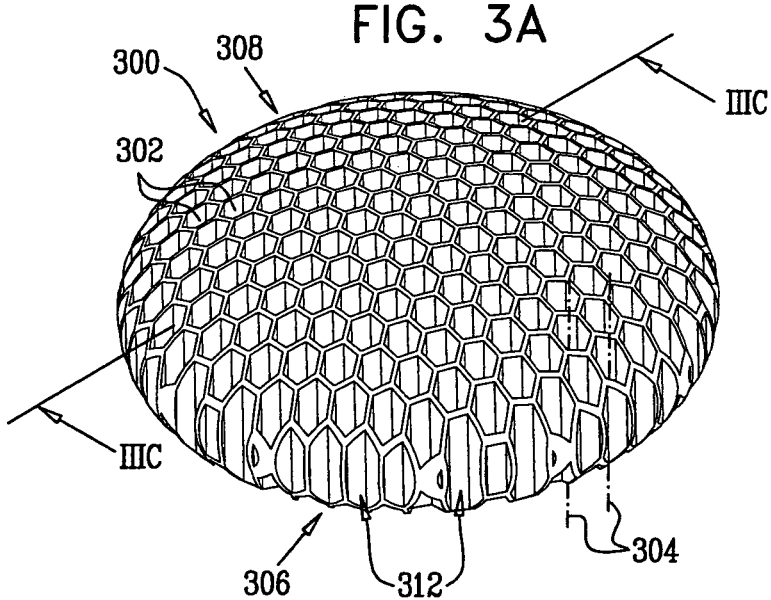
FIGS. 3A, 3B, 3C and 3D are, respectively, pictorial top view, pictorial bottom view, first sectional and second sectional illustrations of an integrally formed internal skeletal element employed in an implantable tissue expander in accordance with yet another preferred embodiment of the present invention.
Figure 3B:
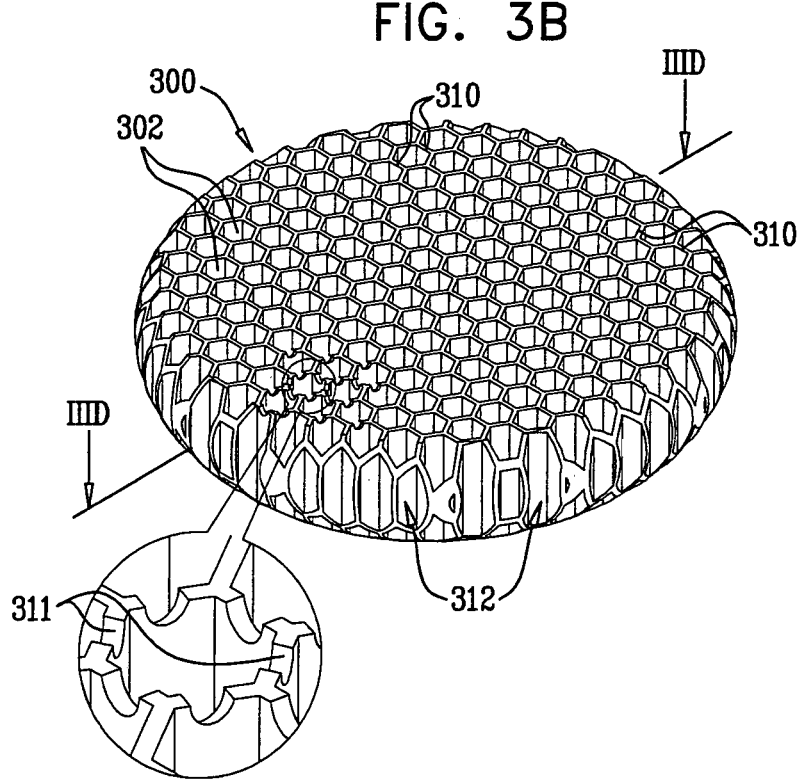
Figure 3C:
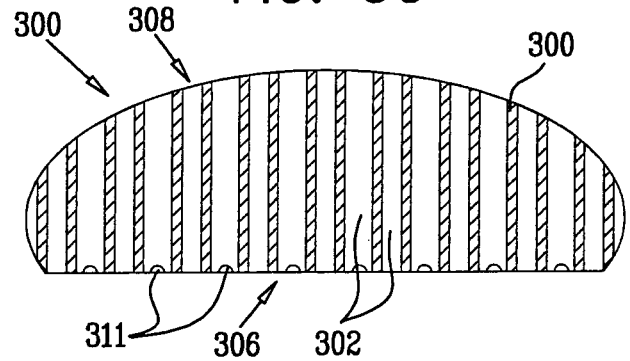
Figure 3D:
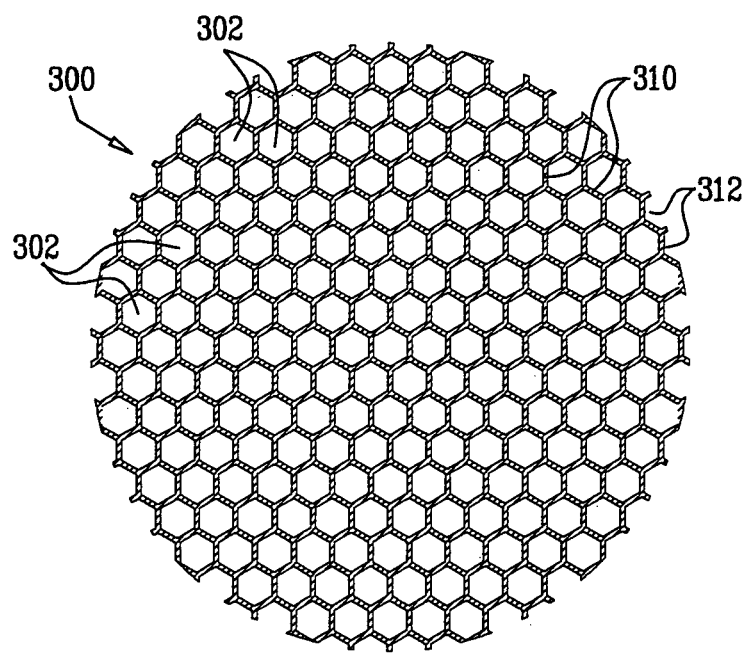

As seen in FIGS. 3A-3D, the integrally formed internal skeletal element 300 includes an array of identical elongate cells 302, each having an hexagonal cross section, extending along mutually generally parallel axes 304 from an imaginary base surface 306, which is typically flat, as in the illustrated embodiment, to an imaginary outer surface 308, which is preferably generally convex and is tucked in adjacent the imaginary base surface 306 as seen clearly in FIGS. 3A-3C. Elongate cells 302 are mutually defined by elongate cell walls 310 formed of a resilient material. Elongate cell walls 310 are preferably formed so as to define fluid passageways 311 communicating between adjacent cells 302.

In the illustrated embodiment, the array of elongate cells 302 is preferably characterized in that elongate cell walls 310 are of generally uniform thickness. It is also characterized in that a regular pattern of partial cells 312 are located along the periphery of the array. In the illustrated embodiment of FIGS. 3A-3D, the partial cells 312 are not identical.

Reference is now made to FIG. 4, which is a sectional illustration of an implantable tissue expander constructed and operative in accordance with a preferred embodiment of the present invention and employing the internal skeletal element 100 of FIGS. 1A-1D. As seen in FIG. 4, the internal skeletal element 100 is enclosed by a peripheral enclosure 400, which preferably includes a generally convex portion 402 which is co-molded with internal skeletal element 100 and a base portion 404 which is polymerized together with the periphery of the convex portion 402 and with the edges of elongate cell walls 110 at imaginary base surface 106 or alternatively sealingly joined thereto by use of a suitable adhesive.

The internal skeletal element 100 and the peripheral enclosure 400 are enclosed by an outer peripheral enclosure 406, which preferably includes a generally convex portion 408 integrally formed with a base portion 410 which are together molded as one piece over peripheral enclosure 400.

Preferably, a tube 412 communicates with the interior of peripheral enclosure 400. The tube is preferably sealed after implantation so as to maintain the interior of the peripheral enclosure 400 at ambient pressure.

It is appreciated that the enclosures employed in various embodiments of the present invention, such as, for example enclosure 400, may be of any suitable thickness. Such thickness may be uniform or varied.

Figure 5:
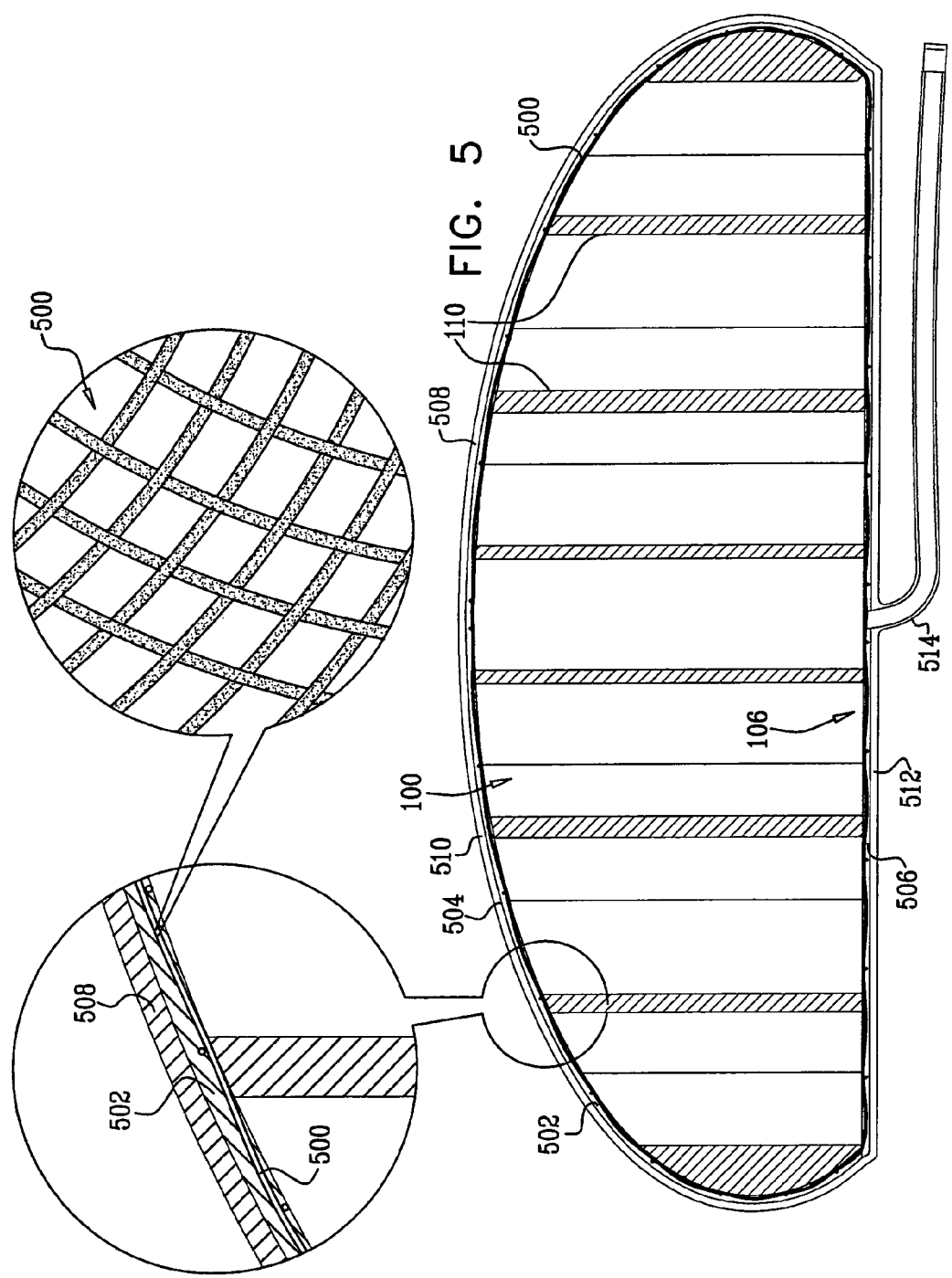
FIG. 5 is a sectional illustration of an implantable tissue expander employing an internal skeletal element and constructed and operative in accordance with another embodiment of the present invention.

Reference is now made to FIG. 5, which is a sectional illustration of an implantable tissue expander constructed and operative in accordance with another preferred embodiment of the present invention and employing the internal skeletal element 100 of FIGS. 1A-1D. In the embodiment of FIG. 5, a mesh 500, preferably formed of highly deformable but minimally stretchable materials, such as polyethylene or polyurethane, surrounds internal skeletal element 100.

As seen in FIG. 5, the internal skeletal element 100 and the mesh 500 are enclosed by a peripheral enclosure 502, which preferably includes a generally convex portion 504 which is co-molded with internal skeletal element 100 over mesh 500. Peripheral enclosure 502 also includes a base portion 506 which is polymerized together with the periphery of the convex portion 504 and with the edges of elongate cell walls 110 at imaginary base surface 106 or alternatively sealingly joined thereto by use of a suitable adhesive.

The internal skeletal element 100 and the mesh 500 are enclosed by an outer peripheral enclosure 508, which preferably includes a generally convex portion 510 integrally formed with a base portion 512 which are together molded as one piece over peripheral enclosure 502 and mesh 500.

Preferably, a tube 514 communicates with the interior of peripheral enclosure 502. The tube is preferably sealed after implantation so as to maintain the interior of the peripheral enclosure 502 at ambient pressure.

Figure 6:
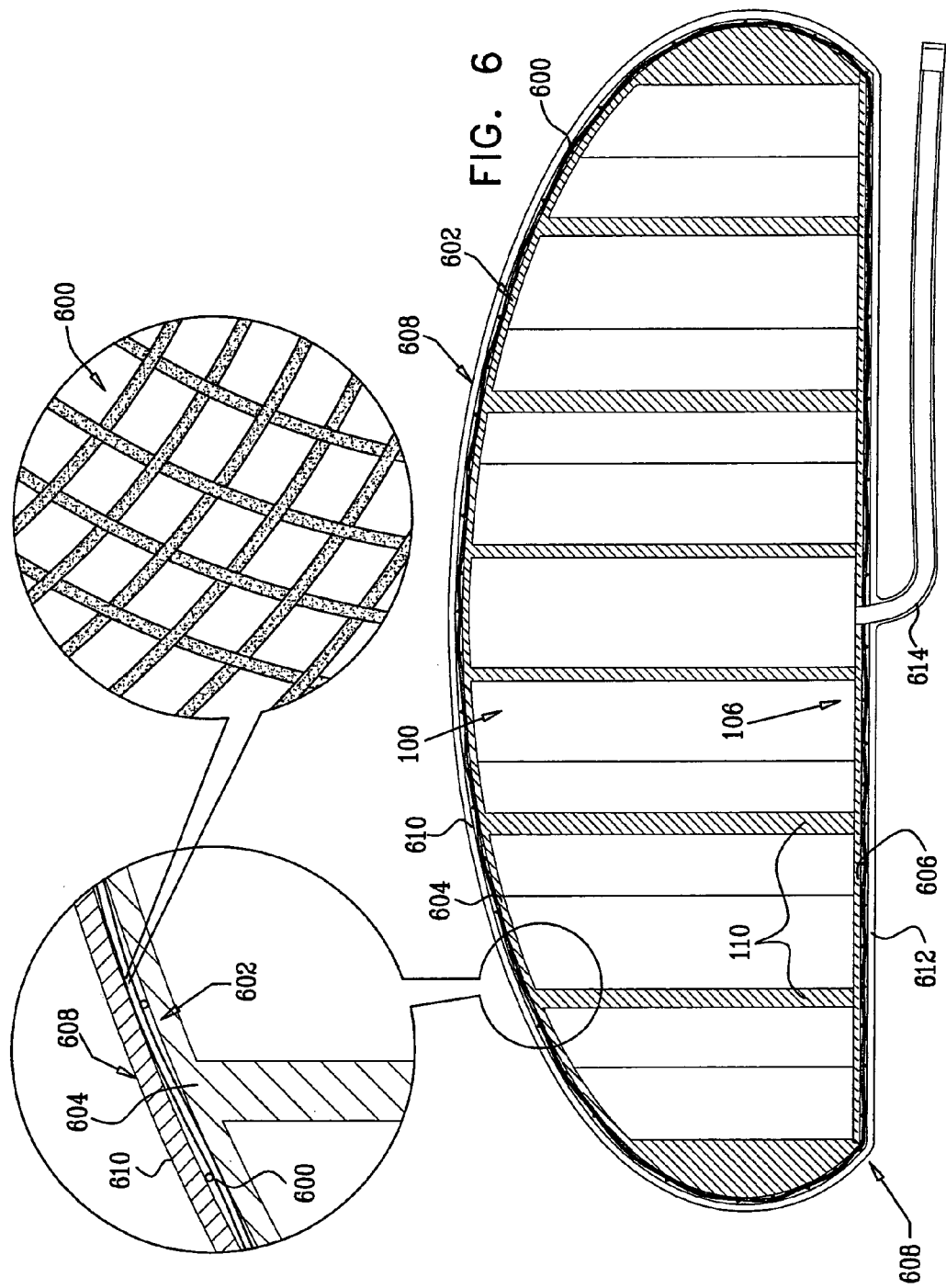
FIG. 6 is a sectional illustration of an implantable tissue expander employing an internal skeletal element and constructed and operative in accordance with yet another embodiment of the present invention.

Reference is now made to FIG. 6, which is a sectional illustration of an implantable tissue expander constructed and operative in accordance with yet another preferred embodiment of the present invention and employing the internal skeletal element 100 of FIGS. 1A-1D. In the embodiment of FIG. 6, a mesh 600, preferably formed of highly deformable but minimally stretchable materials, such as polyethylene or polyurethane, surrounds internal skeletal element 100 and a peripheral enclosure 602.

As seen in FIG. 6, the internal skeletal element 100 is enclosed by peripheral enclosure 602, which preferably includes a generally convex portion 604 which is co-molded with internal skeletal element 100 and a base portion 606 which is polymerized together with the periphery of the convex portion 604 and with the edges of elongate cell walls 110 at imaginary base surface 106 or alternatively sealingly joined thereto by use of a suitable adhesive.

The internal skeletal element 100 and the mesh 600 are enclosed by an outer peripheral enclosure 608, which preferably includes a generally convex portion 610 integrally formed with a base portion 612 which are together molded as one piece over peripheral enclosure 602 and mesh 600.

Preferably, a tube 614 communicates with the interior of peripheral enclosure 602. The tube is preferably sealed after implantation so as to maintain the interior of the peripheral enclosure 602 at ambient pressure.

Figure 7:
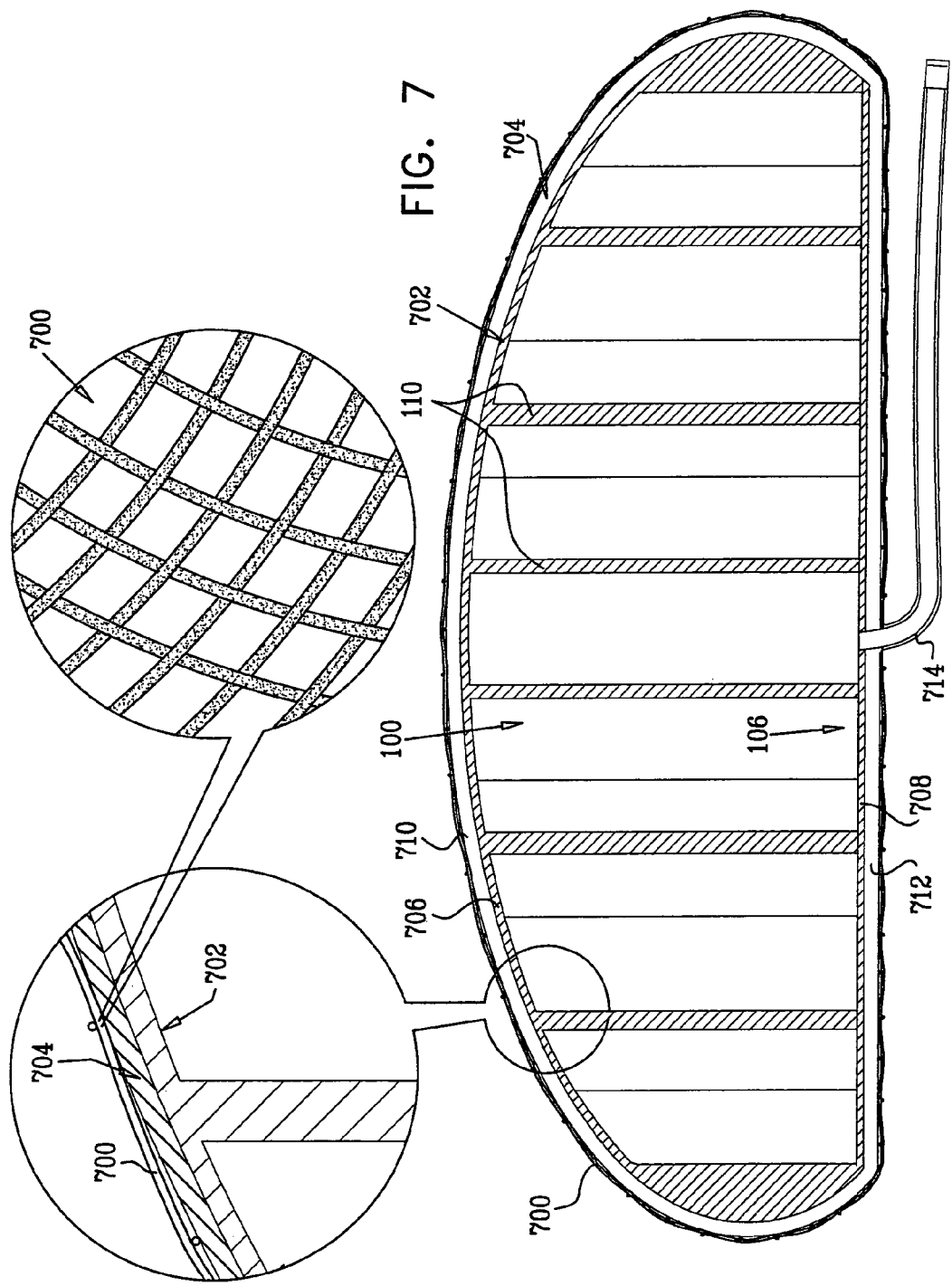
FIG. 7 is a sectional illustration of an implantable tissue expander employing an internal skeletal element and constructed and operative in accordance with yet another embodiment of the present invention.

Reference is now made to FIG. 7, which is a sectional illustration of an implantable tissue expander constructed and operative in accordance with still another preferred embodiment of the present invention and employing the internal skeletal element 100 of FIGS. 1A-1D. In the embodiment of FIG. 7, a mesh 700, preferably formed of highly deformable but minimally stretchable materials, such as polyethylene or polyurethane, surrounds internal skeletal element 100 and first and second peripheral enclosures 702 and 704. Mesh 700 may be entirely external of enclosure 704 and may or may not be attached thereto. Alternatively mesh 700 may be wholly or partially integrated within peripheral enclosure 704.

As seen in FIG. 7, the internal skeletal element 100 is enclosed by first peripheral enclosure 702, which preferably includes a generally convex portion 706 which is co-molded with internal skeletal element 100 and a base portion 708 which is polymerized together with the periphery of the convex portion 706 and with the edges of elongate cell walls 110 at imaginary base surface 106 or alternatively sealingly joined thereto by use of a suitable adhesive. First peripheral enclosure 702 is preferably enclosed by second, outer peripheral enclosure 704, which preferably includes generally convex portion 710 integrally formed with base portion 712 which are together molded as one piece over first peripheral enclosure 702.

Preferably, a tube 714 communicates with the interior of peripheral enclosure 702. The tube is preferably sealed after implantation so as to maintain the interior of first peripheral enclosure 702 at ambient pressure.

Figure 8:
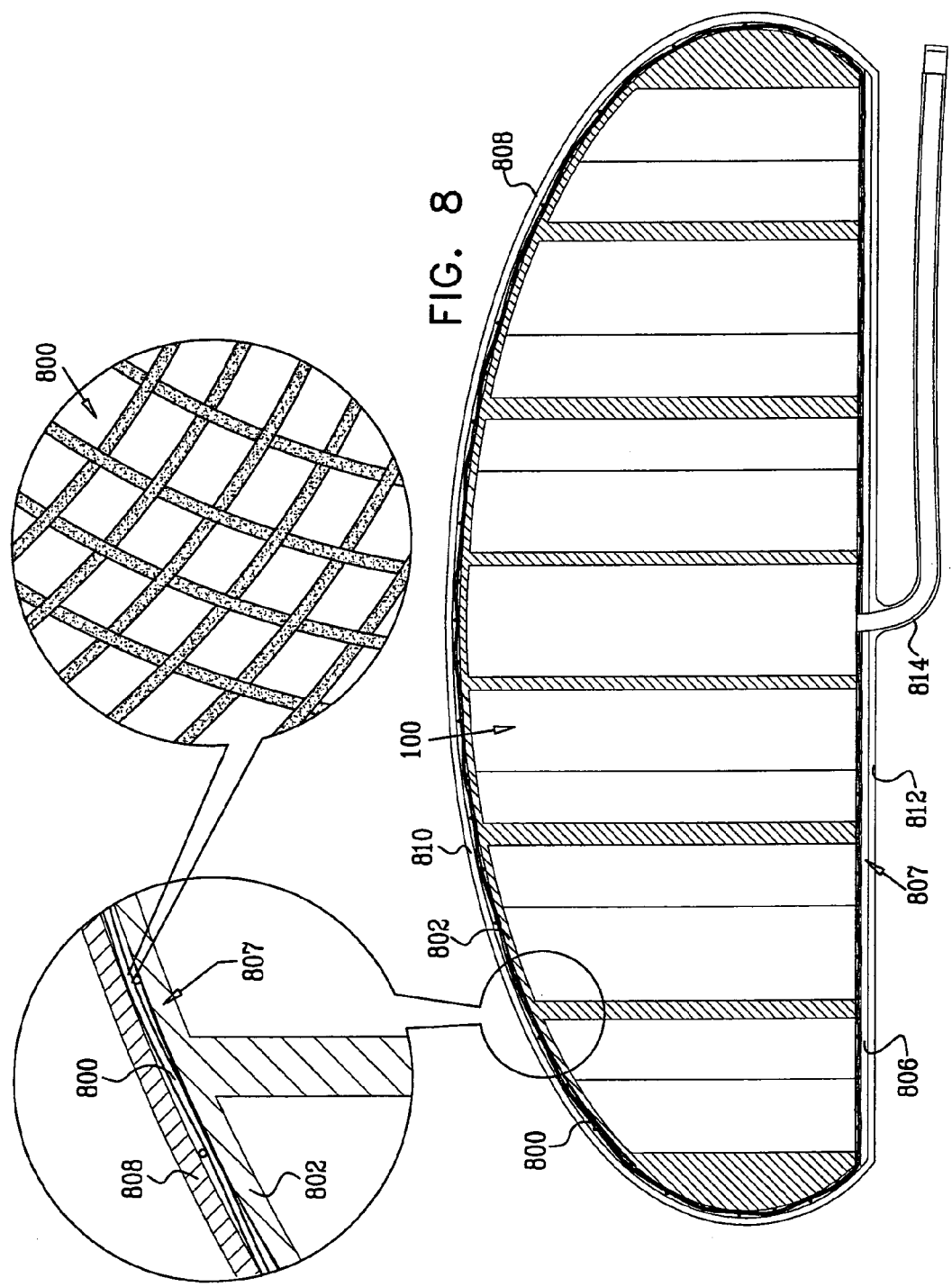
FIG. 8 is a sectional illustration of an implantable tissue expander employing an internal skeletal element and constructed and operative in accordance with still another embodiment of the present invention.

Reference is now made to FIG. 8, which is a sectional illustration of an implantable tissue expander constructed and operative in accordance with yet another preferred embodiment of the present invention and employing the internal skeletal element 100 of FIGS. 1A-1D. In the embodiment of FIG. 8, a mesh 800, preferably formed of highly deformable but minimally stretchable materials, such as polyethylene or polyurethane, surrounds internal skeletal element 100 and a generally convex portion 802.

As seen in FIG. 8, the internal skeletal element 100 is partially enclosed by generally convex portion 802, which is co-molded with internal skeletal element 100. The internal skeletal element 100 and the generally convex portion 802 are fully enclosed by mesh 800. A base portion 806 is polymerized together with the periphery of the convex portion 802 and with the edges of elongate cell walls 110 over mesh 800 at imaginary base surface 106 or alternatively sealingly joined thereto by use of a suitable adhesive, thereby defining a first peripheral enclosure 807.

First peripheral enclosure 807 is preferably enclosed by a second, outer peripheral enclosure 808, which preferably includes a generally convex portion 810 integrally formed with a base portion 812 which are together molded as one piece over first peripheral enclosure 807. It is appreciated that attachment of base portion 806 to convex portion 802 may occur prior to or in the same molding process as that which produces the second peripheral enclosure 808. As a third alternative, either base portion 806 or base portion 812 may be obviated.

Preferably, a tube 814 communicates with the interior of first peripheral enclosure 804. The tube is preferably sealed after implantation so as to maintain the interior of the first peripheral enclosure 804 at ambient pressure.

Figure 9:
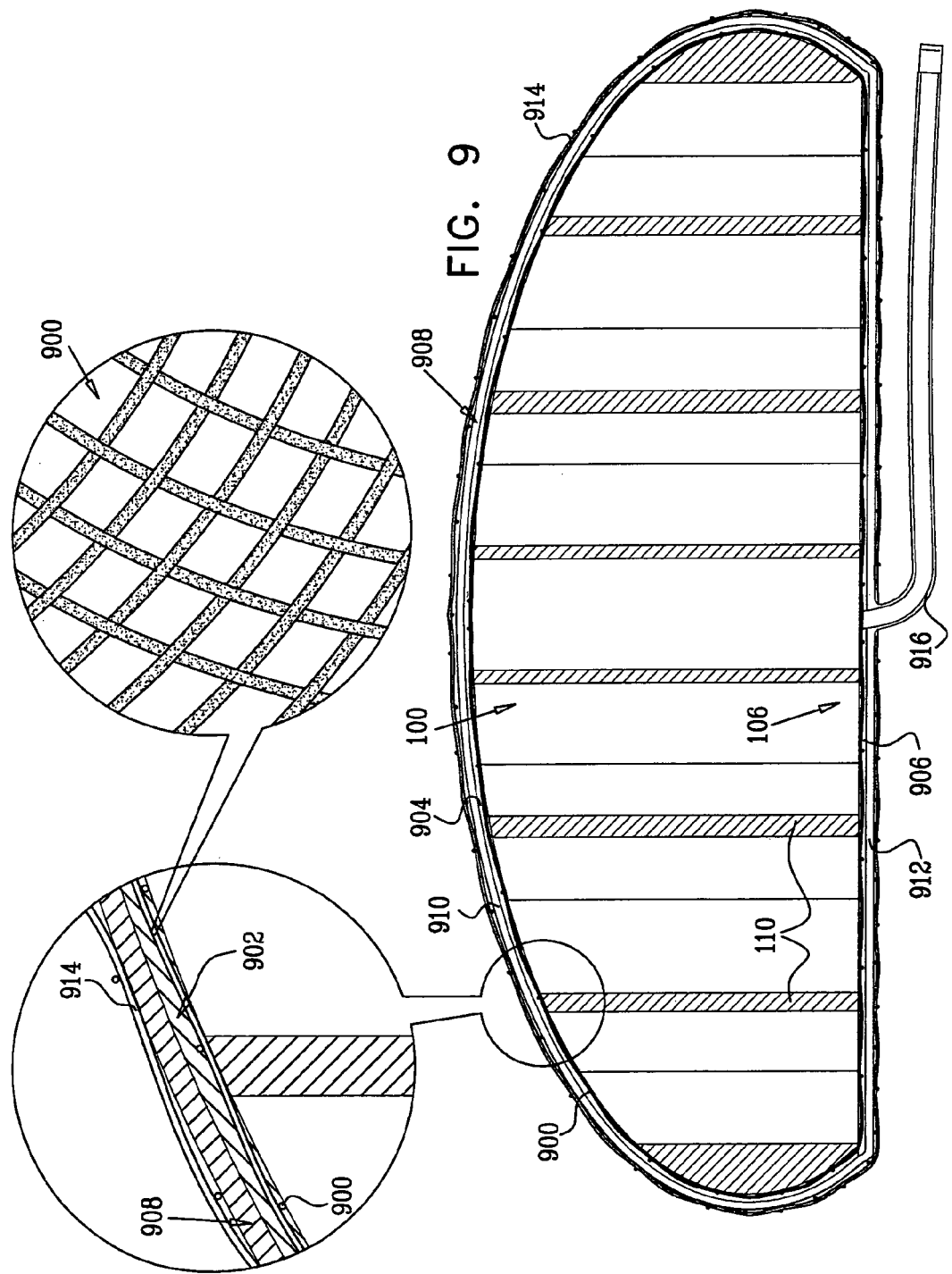
FIG. 9 is a sectional illustration of an implantable tissue expander employing an internal skeletal element and constructed and operative in accordance with yet another embodiment of the present invention.

Reference is now made to FIG. 9, which is a sectional illustration of an implantable tissue expander constructed and operative in accordance with still another preferred, embodiment of the present invention and employing the internal skeletal element 100 of FIGS. 1A-1D. In the embodiment of FIG. 9, a first mesh 900, preferably formed of highly deformable but minimally stretchable materials, such as polyethylene or polyurethane, surrounds internal skeletal element 100. The term "mesh" is used in a broad sense to cover any type of open enclosure, such as a fabric enclosure, which may be woven or non-woven and may have regular or irregularly shaped and spaced openings. A mesh may be formed of a single piece or multiple pieces or strands of material in any suitable manner, such as for example, by injection molding, winding or wrapping.

As seen in FIG. 9, the internal skeletal element 100 and first mesh 900 are enclosed by a peripheral enclosure 902, which preferably includes a generally convex portion 904 which is co-molded with internal skeletal element 100 over first mesh 900. Peripheral enclosure 902 also includes a base portion 906 which is polymerized together with the periphery of the convex portion 904 and with the edges of elongate cell walls 110 at imaginary base surface 106 or alternatively sealingly joined thereto by use of a suitable adhesive.

The internal skeletal element 100 and first mesh 900 are enclosed by an outer peripheral enclosure 908, which preferably includes a generally convex portion 910 integrally formed with a base portion 912 which are together molded as one piece over peripheral enclosure 902 and first mesh 900.

A second mesh 914 is preferably formed or wrapped around the outer peripheral enclosure 908. Preferably, a tube 916 communicates with the interior of peripheral enclosure 902. The tube is preferably sealed after implantation so as to maintain the interior of the peripheral enclosure 902 at ambient pressure.

Figure 10:
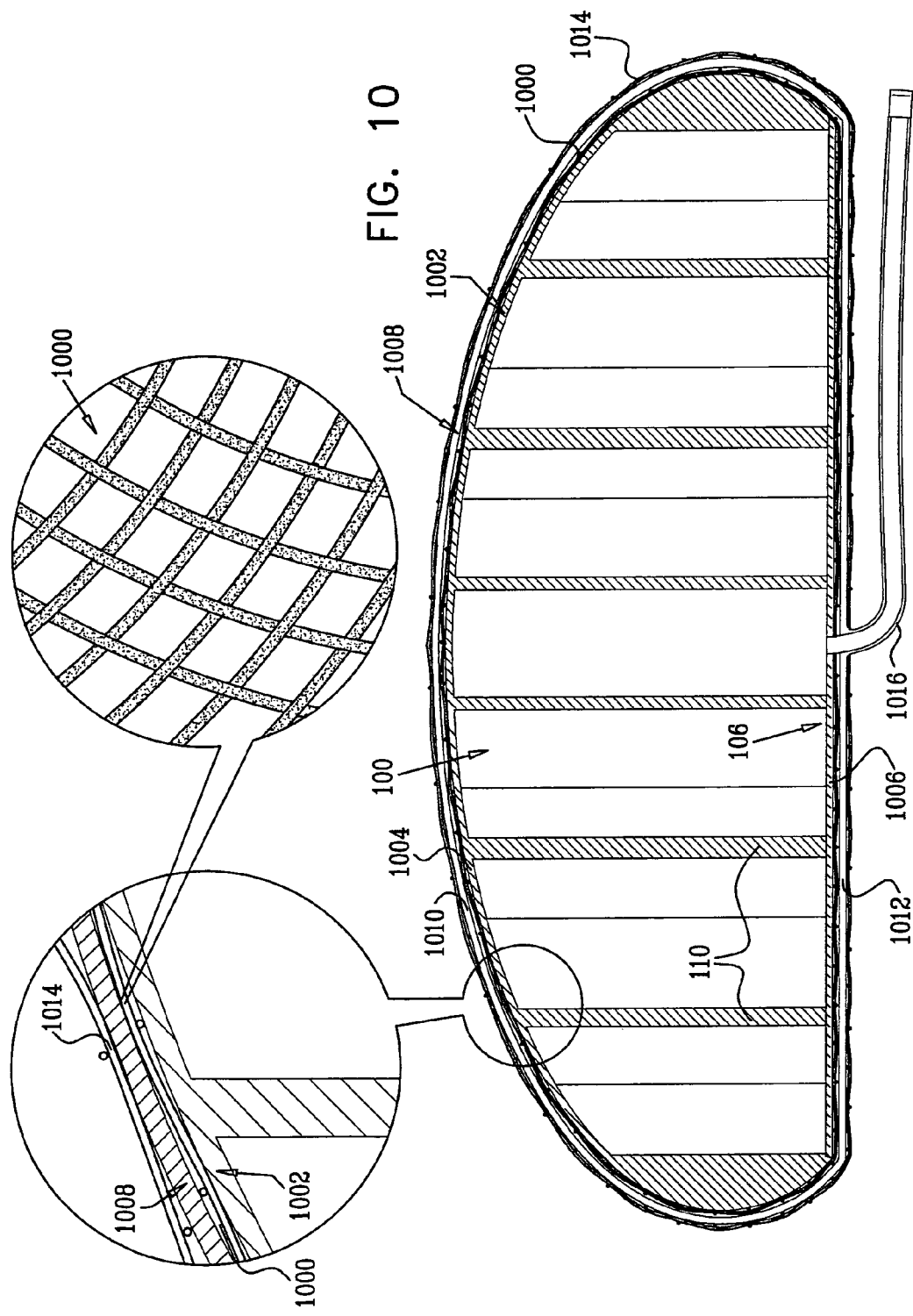
FIG. 10 is a sectional illustration of an implantable tissue expander employing an internal skeletal element and constructed and operative in accordance with still another embodiment of the present invention.

Reference is now made to FIG. 10, which is a sectional illustration of an implantable tissue expander constructed and operative in accordance with yet a further preferred embodiment of the present invention and employing the internal skeletal element 100 of FIGS. 1A-1D. In the embodiment of FIG. 10, a first mesh 1000, preferably formed of highly deformable but minimally stretchable materials, such as polyethylene or polyurethane, surrounds internal skeletal element 100 and a peripheral enclosure 1002.

As seen in FIG. 10, the internal skeletal element 100 is enclosed by peripheral enclosure 1002, which preferably includes a generally convex portion 1004 which is co-molded with internal skeletal element 100 and a base portion 1006 which is polymerized together with the periphery of the convex portion 1004 and with the edges of elongate cell walls 110 at imaginary base surface 106 or alternatively sealingly joined thereto by use of a suitable adhesive.

The internal skeletal element 100 and the first mesh 1000 are enclosed by an outer peripheral enclosure 1008, which preferably includes a generally convex portion 1010 integrally formed with a base portion 1012 which are together molded as one piece over peripheral enclosure 1002 and mesh 1000.

A second mesh 1014 is preferably formed or wrapped around the outer peripheral enclosure 1008. Preferably, a tube 1016 communicates with the interior of peripheral enclosure 1002. The tube is preferably sealed after implantation so as to maintain the interior of the peripheral enclosure 1002 at ambient pressure.

Figure 11:
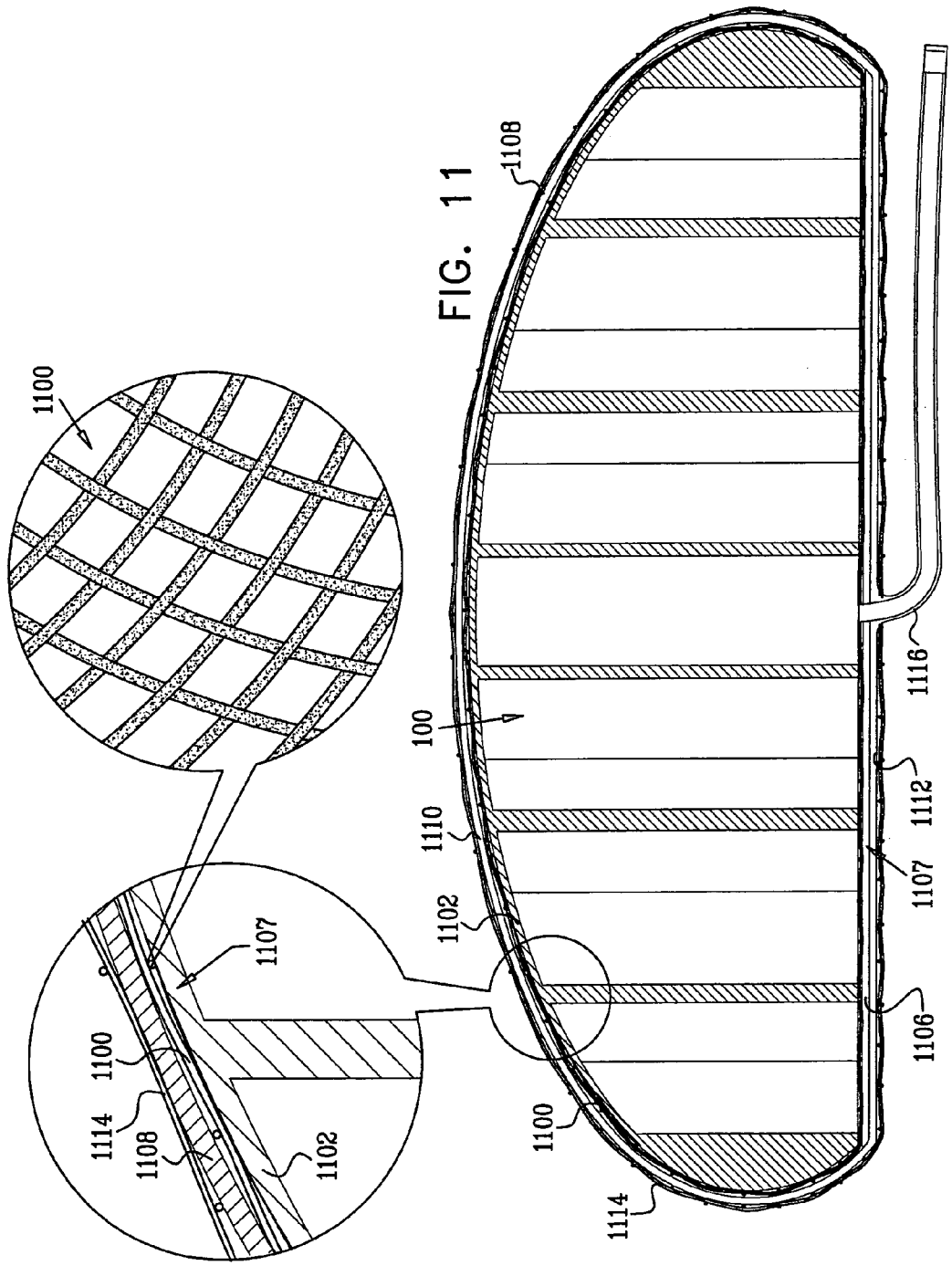
FIG. 11 is a sectional illustration of an implantable tissue expander employing an internal skeletal element and constructed and operative in accordance with yet another embodiment of the present invention.

Reference is now made to FIG. 11, which is a sectional illustration of an implantable tissue expander constructed and operative in accordance with still another preferred embodiment of the present invention and employing the internal skeletal element 100 of FIGS. 1A-1D. In the embodiment of FIG. 11, a first mesh 1100, preferably formed of highly deformable but minimally stretchable materials, such as polyethylene or polyurethane, surrounds internal skeletal element 100 and a generally convex portion 1102.

As seen in FIG. 11, the internal skeletal element 100 is partially enclosed by generally convex portion 1102, which is co-molded with internal skeletal element 100. The internal skeletal element 100 and the generally convex portion 1102 are fully enclosed by first mesh 1100. A base portion 1106 is polymerized together with the periphery of the convex portion 1102 and with the edges of elongate cell walls 110 over mesh 1100 at imaginary base surface 106 or alternatively sealingly joined thereto by use of a suitable adhesive, thereby defining a first peripheral enclosure 1107.

First peripheral enclosure 1107 is preferably enclosed by a second, outer peripheral enclosure 1108, which preferably includes a generally convex portion 1110 integrally formed with a base portion 1112 which are together molded as one piece over first peripheral enclosure 1107. It is appreciated that attachment of base portion 1106 to convex portion 1102 may occur prior to or in the same molding process as that which produces the second peripheral enclosure 1108. As a third alternative, either base portion 1106 or base portion 1112 may be obviated.

A second mesh 1114 is preferably formed or wrapped around the outer peripheral enclosure 1108. Preferably, a tube 1116 communicates with the interior of peripheral enclosure 1102. The tube is preferably sealed after implantation so as to maintain the interior of the peripheral enclosure 1102 at ambient pressure.

Reference is now made to FIG. 12, which is a simplified illustration of a method of manufacturing the implantable tissue expander of FIG. 4. As seen in FIG. 12, the internal skeletal element 100 and the generally convex portion 402 of peripheral enclosure 400 are co-molded as one piece as seen at stages designated A, B and C. Thereafter, in a subsequent separate molding stage, designated D, base portion 404 is formed and polymerized together with the periphery of the convex portion 402 and with the edges of elongate cell walls 110 at imaginary base surface 106. Thereafter, in a subsequent separate molding stage designated E, outer peripheral enclosure 406 is formed over peripheral enclosure 404. Tube 412 (not shown) may also be formed in molding stage E.

Figure 13A:
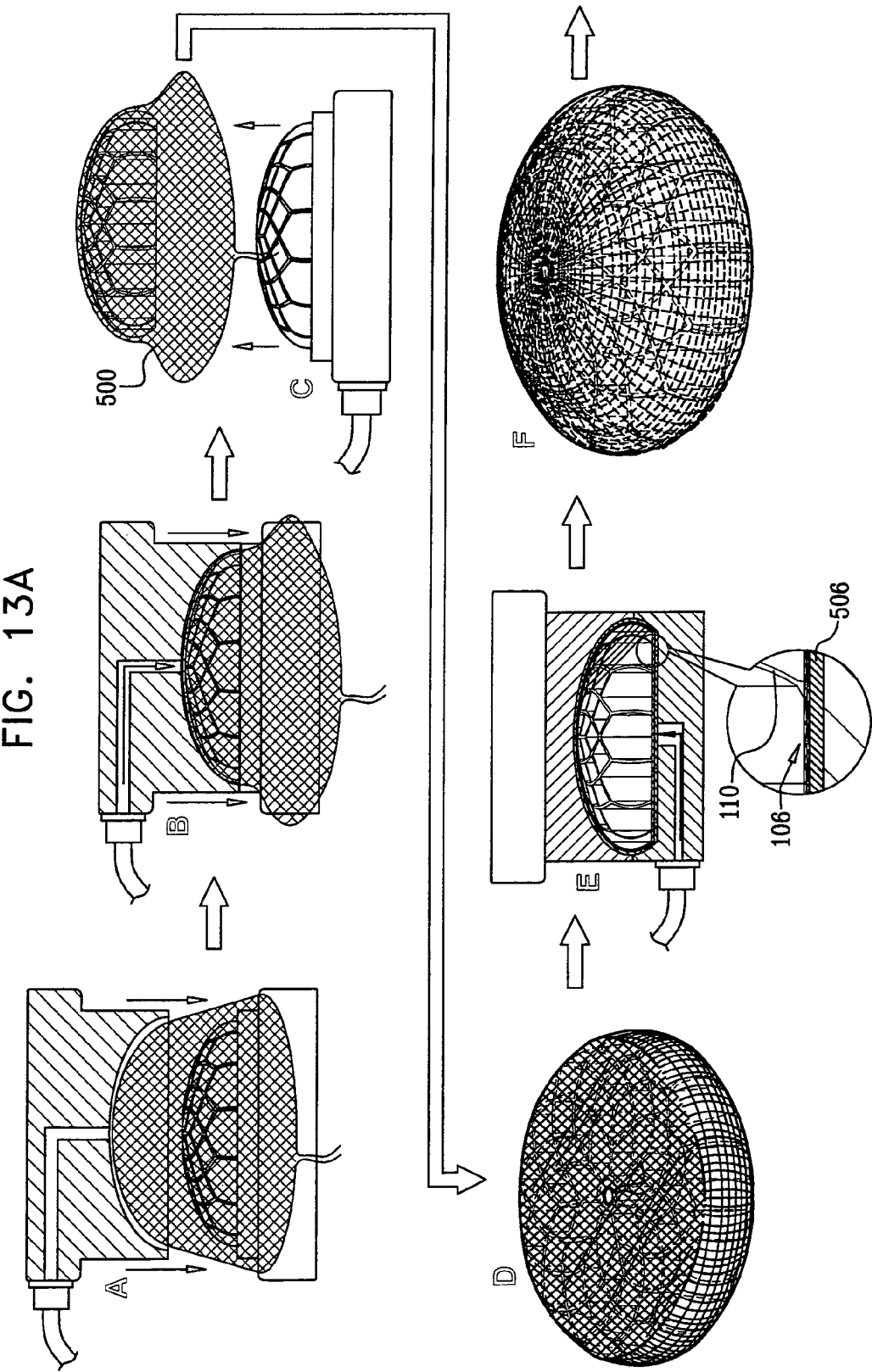

Reference is now made to FIGS. 13A & 13B, which together are a simplified illustration of a method of manufacturing the implantable tissue expander of FIG. 5. As seen in FIGS. 13A & 13B, the internal skeletal element 100 and the generally convex portion 504 of peripheral enclosure 502 are co-molded as one piece over mesh 500 as seen at stages designated A, B and C. Thereafter, the mesh 500 is fitted over the internal skeletal element 100 at the imaginary base surface 106 and fixed in position, preferably without folding of the mesh, as shown at stage D. In a subsequent separate molding stage, designated E, base portion 506 is formed and polymerized together with the periphery of the convex portion 504 and with the edges of elongate cell walls 110 at imaginary base surface 106. Tube 514 (not shown) may also be formed in molding stage E.

In a subsequent separate molding stage, designated G, the outer peripheral enclosure 508 is molded as one piece over inner peripheral enclosure 502.

Figure 14B:
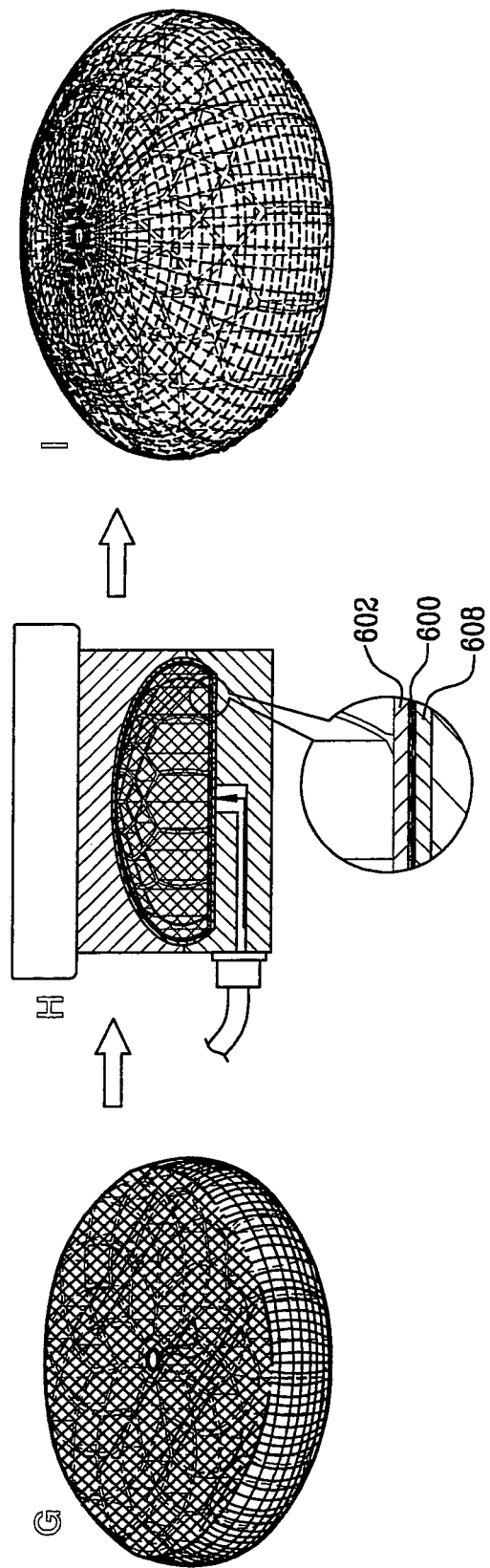

Reference is now made to FIGS. 14A & 14B, which together are a simplified illustration of a method of manufacturing the implantable tissue expander of FIG. 6. As seen in FIGS. 14A & 14B, the internal skeletal element 100 and the generally convex portion 604 of peripheral enclosure 602 are co-molded as one piece as seen at stages designated A, B and C. Thereafter, in a subsequent separate molding stage, designated D, base portion 606 is formed and polymerized together with the periphery of the convex portion 604 and with the edges of elongate cell walls 110 at imaginary base surface 106. Tube 614 (not shown) may also be formed in molding stage D.

Thereafter, mesh 600 is fitted over the internal skeletal element 100 at the imaginary base surface 106 and fixed in position, preferably without folding of the mesh, as shown at stage F. In a subsequent separate molding stage, designated H, the outer peripheral enclosure 608 is molded as one piece over peripheral enclosure 602 and mesh 600.

Figure 15A:
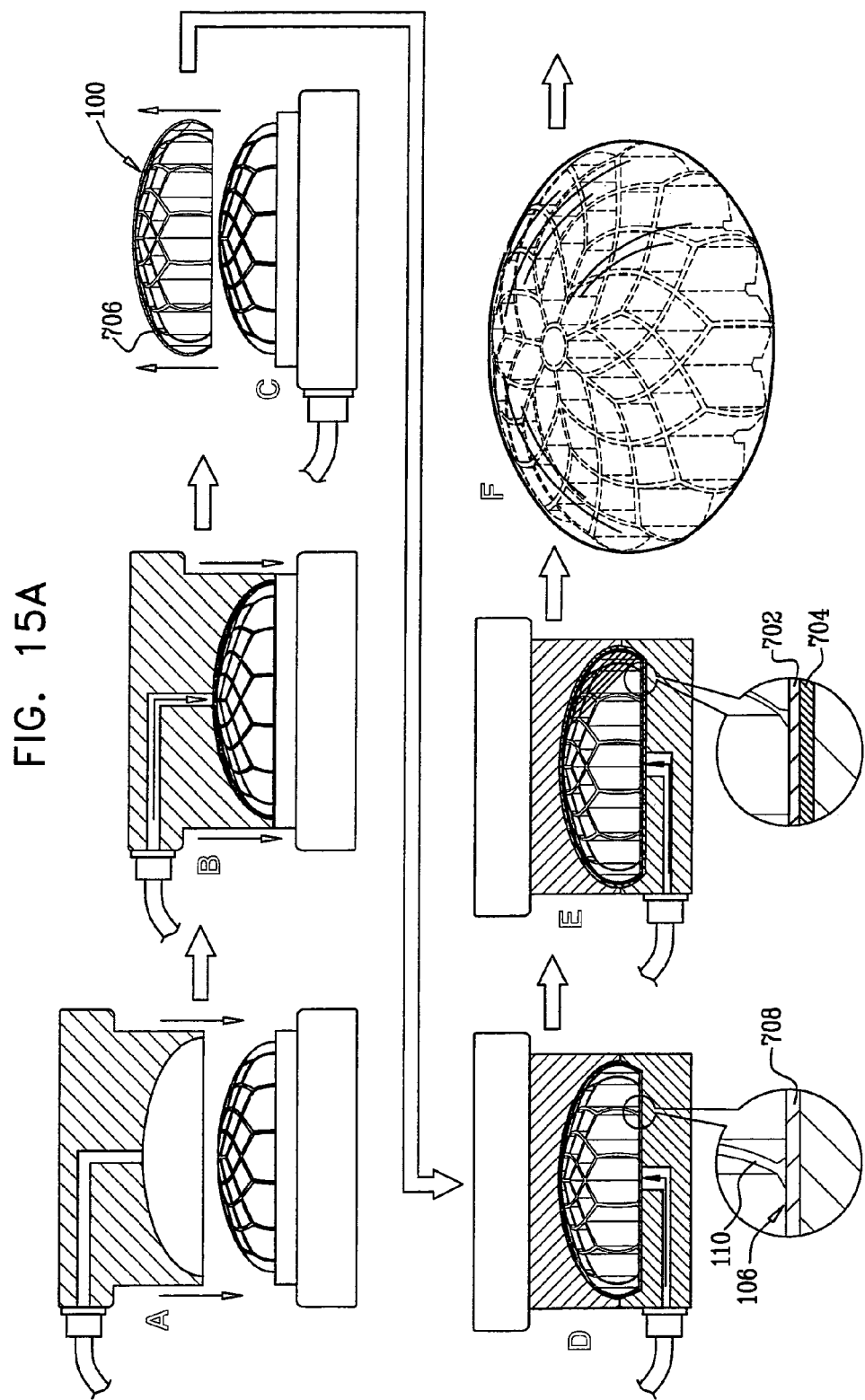

Reference is now made to FIGS. 15A & 15B, which together are a simplified illustration of a method of manufacturing the implantable tissue expander of FIG. 7. As seen in FIGS. 15A & 15B, the internal skeletal element 100 and the generally convex portion 706 of first peripheral enclosure 702 are co-molded as one piece as seen at stages designated A, B and C. Thereafter, in a subsequent separate molding stage, designated D, base portion 708 is formed and polymerized together with the periphery of the convex portion 706 and with the edges of elongate cell walls 110 at imaginary base surface 106. Tube 714 (not shown) may also be formed in molding stage D.

In a subsequent separate molding stage, designated E, the outer peripheral enclosure 704 is molded as one piece over first peripheral enclosure 702.

Thereafter, the mesh 700 is fitted over the outer peripheral enclosure 708 and fixed in position, preferably without folding of mesh 700 as shown at stage G.

Reference is now made to FIG. 16, which is a simplified illustration of a method of manufacturing the implantable tissue expander of FIG. 8 in accordance with another embodiment of the present invention. Internal skeletal element 100 is integrally formed with generally convex portion 802 forming part of first peripheral enclosure 807, in a manner which may be identical to the formation of internal skeletal element 100 and the generally convex portion 402 of peripheral enclosure 400 shown in FIG. 12 at stages designated A, B and C and described hereinabove.

As shown at a stage designated B, the integrally formed internal skeletal element 100 and generally convex portion 802 are then temporarily and resiliently deformed to fit within mesh 800, here shaped generally to conform to the outer surface of convex portion 802. The mesh 800 surrounds the integrally formed internal skeletal element 100 and generally convex portion 802 and is retained in position with respect thereto. The mesh 800 is fitted over the internal skeletal element 100 at the imaginary base surface 106 and fixed in position, preferably without folding of mesh 800, as shown at stage C.

Thereafter, in a subsequent separate molding stage, designated D, outer peripheral enclosure 808 is formed over first peripheral enclosure 807. Tube 814 (not shown) may also be formed in molding stage D.

It is appreciated that attachment of base portion 806 to convex portion 802 may occur prior to or in the same molding process as that which produces the second peripheral enclosure 808. As a third alternative, either base portion 806 or base portion 812 may be obviated.

Figure 17:
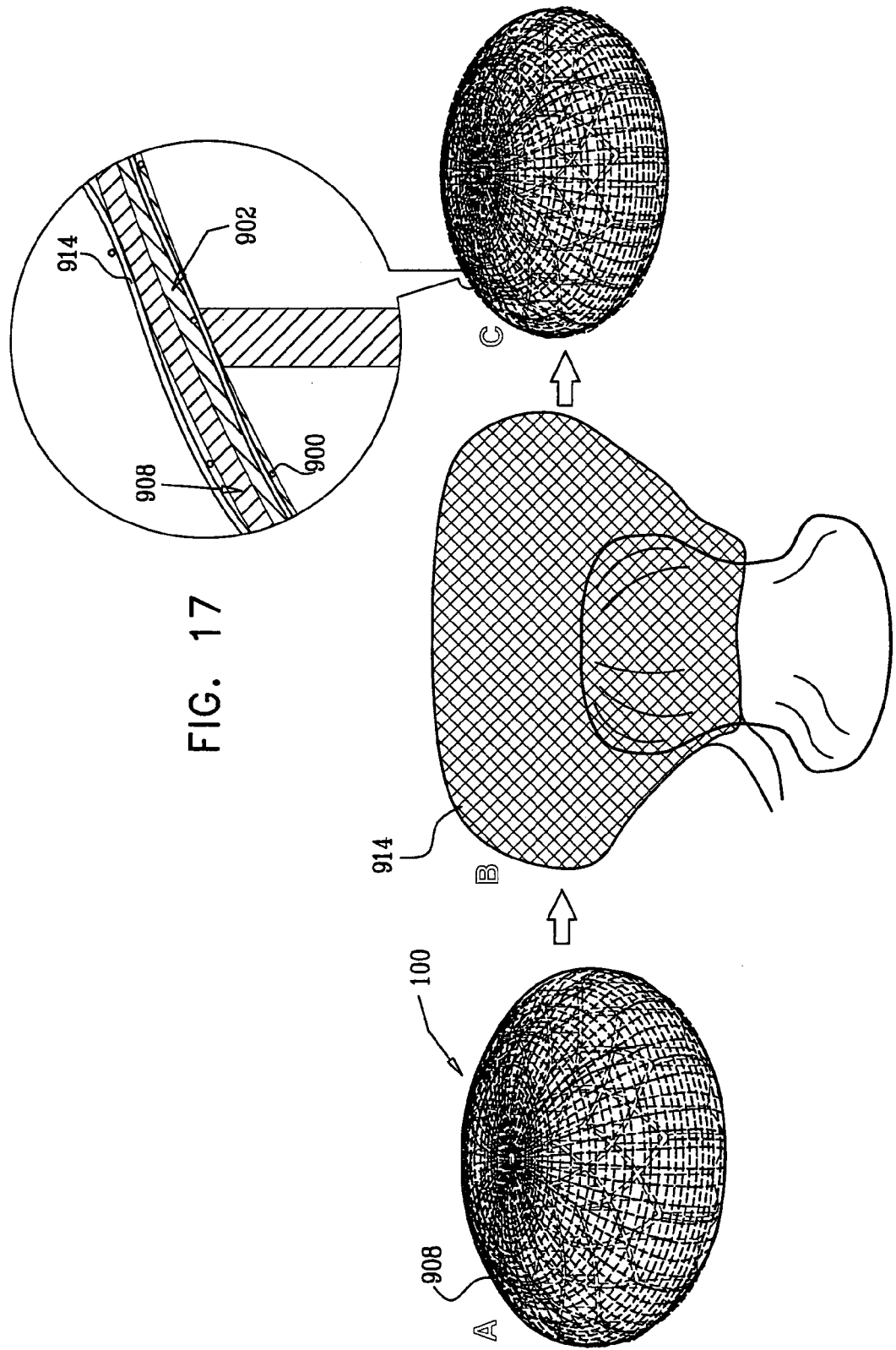
FIG. 17 is a simplified illustration of a method of manufacturing the implantable tissue expander of FIG. 9 in accordance with a still further embodiment of the present invention.

Reference is now made to FIG. 17, which is a simplified illustration of a method of manufacturing the implantable tissue expander of FIG. 9 in accordance with another embodiment of the present invention. Internal skeletal element 100 is formed with first mesh 900, peripheral enclosure 902 and outer peripheral enclosure 908 in a manner which may be identical to the formation of internal skeletal element 100 and peripheral enclosures 502 and 508 as shown in FIGS. 13A and 13B at stages designated A-H and described hereinabove.

As shown at a stage designated B, the internal skeletal element 100, first mesh 900 and peripheral enclosures 902 and 908 are then temporarily and resiliently deformed to fit within second mesh 914, here shaped generally to conform to the outer surface of outer peripheral enclosure 908. Second mesh 914 surrounds the integrally formed internal skeletal element 100 and outer peripheral enclosure 908 and is retained in position with respect thereto.

Figure 18:
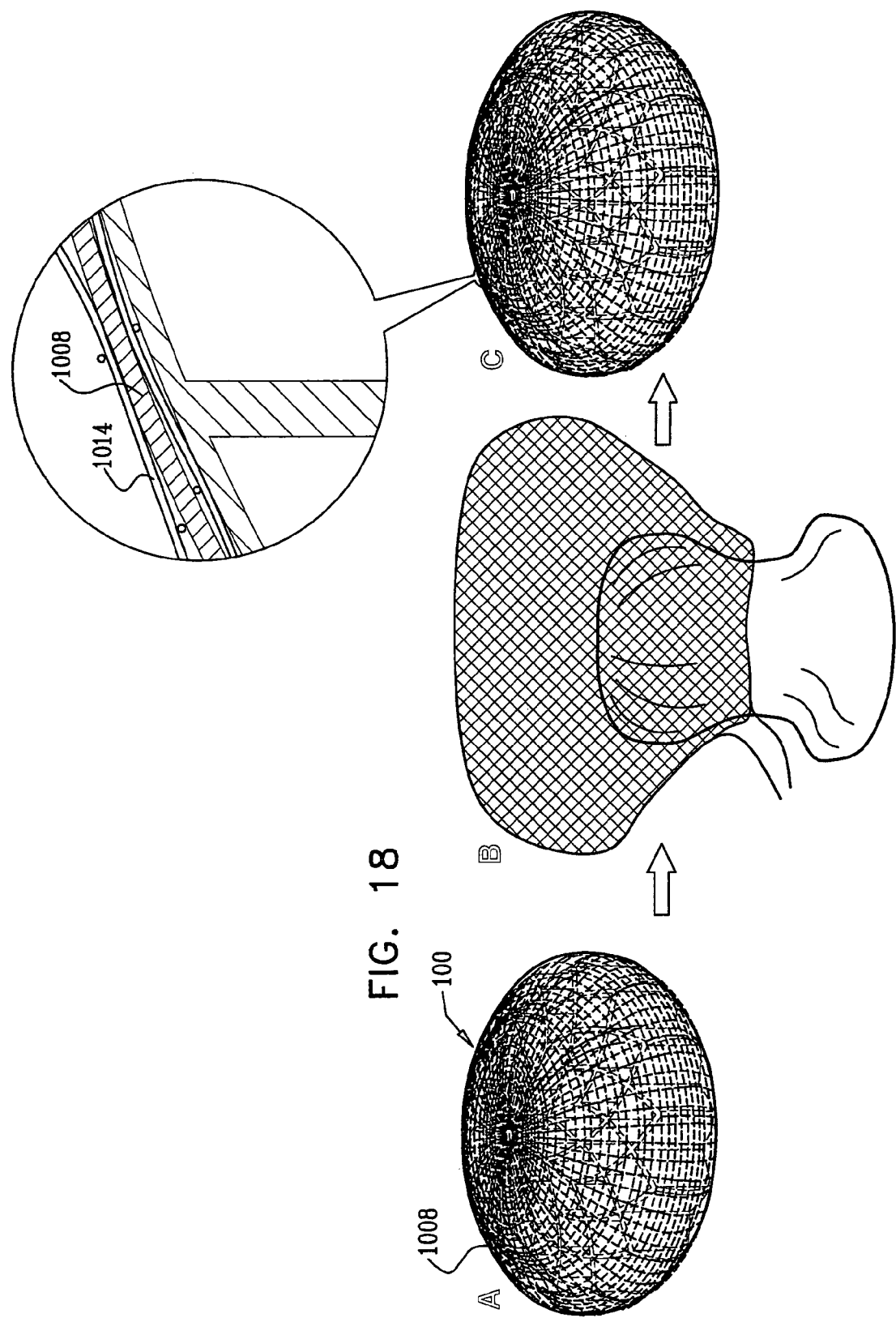
FIG. 18 is a simplified illustration of a method of manufacturing the implantable tissue expander of FIG. 10 in accordance with yet a further embodiment of the present invention.

Reference is now made to FIG. 18, which is a simplified illustration of a method of manufacturing the implantable tissue expander of FIG. 10. Following the methodology of stages A-H of FIGS. 14A & 14B, described hereinabove, second mesh 1014 is preferably formed or wrapped around the outer peripheral enclosure 1008, preferably without folding of the mesh.

Figure 19:
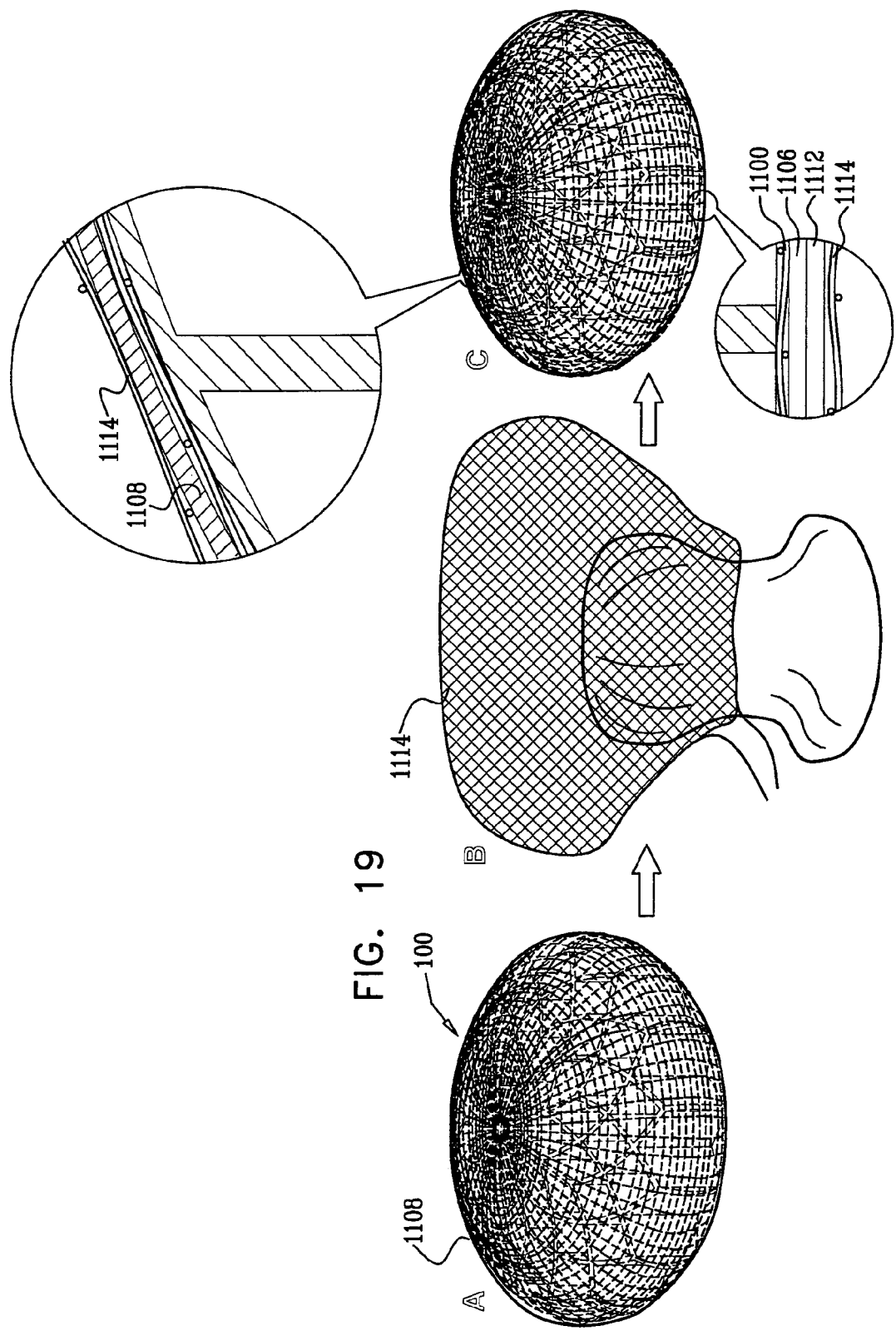
FIG. 19 is a simplified illustration of a method of manufacturing the implantable tissue expander of FIG. 11 in accordance with another embodiment of the present invention.

Reference is now made to FIG. 19, which is a simplified illustration of a method of manufacturing the implantable tissue expander of FIG. 11. Following the methodology of stages A-E of FIG. 16, described hereinabove, second mesh 1114 is preferably formed or wrapped around the outer peripheral enclosure 1108, preferably without folding of second mesh 1114.

It will be appreciated by persons skilled in the art that the present invention is not limited to what has been particularly shown and described hereinabove. Rather the scope of the present invention includes both combinations and subcombinations of various feature described hereinabove as well as modifications and variations thereof which would occur to a person skilled in the art upon reading the foregoing description and which are not in the prior art.

The invention claimed is:

1. An implantable tissue expander comprising:
an integrally formed, resiliently deformable, internal skeletal element extending between a flat base surface and an outer surface, the outer surface having a convex shape encompassing the entire outer surface, and including at least one plurality of non-random elongate cells extending longitudinally along mutually parallel axes from said base surface to said outer surface and being defined by elongate cell walls formed of a resilient human-implantable material; and
a sealed enclosure, sealing said internal skeletal element and configured to prevent body fluids from filling said plurality of non-random elongate cells; wherein the skeletal element is temporarily and resiliently deformable in that after being deformed to reduced dimensions, the base and the outer surface are able to regain their flat and convex configurations, respectively, by virtue of the resiliency of the skeletal element.

2. An implantable tissue expander according to claim 1 and wherein said at least one plurality of non-random elongate cells comprises at least first and second pluralities of non-random elongate cells extending over correspondingly different mutually generally parallel axes from said base surface to said outer surface.

3. An implantable tissue expander according to claim 1 and wherein said at least one plurality of non-random elongate cells comprises a single plurality of non-random elongate cells extending over mutually parallel axes from said base surface to said outer surface.

4. An implantable tissue expander according to claim 1, and wherein said elongate cell walls define fluid passageways communicating between adjacent cells in said at least one plurality of non-random elongate cells.

5. An implantable tissue expander according to claim 1, and wherein said at least one plurality of non-random elongate cells includes a central cylindrical cell.

6. An implantable tissue expander according to claim 1, and wherein said elongate cell walls are of uniform thickness.

7. An implantable tissue expander according to claim 1, and wherein said at least one plurality of non-random elongate cells includes partial cells located along a periphery thereof.

8. An implantable tissue expander according to claim 7 and wherein said partial cells are identical.

9. An implantable tissue expander according to claim 1, and wherein said at least one plurality of non-random elongate cells have a hexagonal cross section.

10. An implantable tissue expander according to claim 1, and also comprising at least one mesh.

11. An implantable tissue expander according to claim 10 and wherein said at least one mesh is formed of a highly deformable, minimally stretchable material.

12. An implantable tissue expander according to claim 10, and wherein said mesh is at least partially integrated with said sealed enclosure.

13. An implantable tissue expander according to claim 10, and wherein said mesh comprises a plurality of layers of mesh.

14. An implantable tissue expander according to claim 13 and wherein at least two layers of mesh are located on opposite sides of at least one layer of said sealed enclosure.

15. An implantable tissue expander according to claim 1, and wherein said sealed enclosure comprises a convex portion and a base portion.

16. An implantable tissue expander according to claim 1, and wherein said sealed enclosure comprises multiple enclosure layers.

17. An implantable tissue expander according to claim 1, and also comprising a tube communicating with an interior of said sealed enclosure.

18. An implantable tissue expander according to claim 1, and wherein said sealed enclosure has non-uniform wall thickness.

19. A method of manufacturing an implantable tissue expander comprising:

forming an integrally formed, resiliently deformable, internal skeletal element, said internal skeletal element extending between a flat base surface and an outer surface, the outer surface having a convex shape encompassing the entire outer surface, and including at least one plurality of non-random elongate cells extending longitudinally along mutually parallel axes from said base surface to said outer surface and being defined by elongate cell walls formed of a resilient human-implantable material; and forming a peripheral enclosure over said internal skeletal element, said peripheral enclosure being operative to seal said internal skeletal element and being adapted to prevent body fluids from filling said plurality of non-random elongate cells; wherein the skeletal element is temporarily and resiliently deformable in that after being deformed to reduced dimensions, the base and the outer surface are able to regain their flat and convex configurations, respectively, by virtue of the resiliency of the skeletal element.

20. A method according to claim 19 and wherein said forming a peripheral enclosure includes forming a base portion of said enclosure and a convex portion of said enclosure and polymerizing said base portion together with a periphery of said convex portion and with edges of said elongate cell walls.

21. A method according to claim 19, and also comprising forming an outer enclosure over said peripheral enclosure.

22. A method according to claim 19, and wherein said forming steps comprises integrally forming said internal skeletal element and a convex portion of said peripheral enclosure over a mesh.

23. A method according to claim 19, and also comprising providing a tube communicating with an interior of said peripheral enclosure.

* * * * *

UNITED STATES PATENT AND TRADEMARK OFFICE
CERTIFICATE OF CORRECTION

PATENT NO.       : 8,545,557 B2                                           Page 1 of 1
APPLICATION NO. : 12/521126
DATED            : October 1, 2013
INVENTOR(S)      : Glicksman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 883 days.

Signed and Sealed this

Fifteenth Day of September, 2015

Michelle K. Lee
*Director of the United States Patent and Trademark Office*